(12) United States Patent
Herscu et al.

(10) Patent No.: US 11,058,456 B2
(45) Date of Patent: Jul. 13, 2021

(54) CATHETER EXTRACTION

(71) Applicant: Qathex, LLC, Livermore, CA (US)

(72) Inventors: Gabriel Herscu, Livermore, CA (US); Curt Toppel, Manhattan Beach, CA (US); Elmer Tolentino, Livermore, CA (US)

(73) Assignee: Qathex, LLC, Livermore, CA (US)

(*) Notice: Subject to any disclaimer, the term of this patent is extended or adjusted under 35 U.S.C. 154(b) by 172 days.

(21) Appl. No.: 16/041,011

(22) Filed: Jul. 20, 2018

(65) Prior Publication Data

US 2018/0325550 A1 Nov. 15, 2018

Related U.S. Application Data

(60) Division of application No. 15/011,341, filed on Jan. 29, 2016, now Pat. No. 10,052,128, which is a
(Continued)

(51) Int. Cl.
*A61B 17/34* (2006.01)
*A61M 25/00* (2006.01)
(Continued)

(52) U.S. Cl.
CPC ........ *A61B 17/3468* (2013.01); *A61B 17/282* (2013.01); *A61B 17/32053* (2013.01);
(Continued)

(58) Field of Classification Search
CPC .......... A61B 17/32053; A61B 17/3205; A61B 17/32002; A61B 17/320783; A61B 17/1659; A61B 17/3468; A61B 17/320016
See application file for complete search history.

(56) References Cited

U.S. PATENT DOCUMENTS

| 4,020,847 A | 5/1977 | Clark, III |
| 5,897,561 A | 4/1999 | Raines |

(Continued)

FOREIGN PATENT DOCUMENTS

| CN | 103327913 B | 9/2015 |
| EP | 2484299 A1 | 8/2012 |
| WO | WO-2017035168 | 2/2017 |

OTHER PUBLICATIONS

"PCT/US2016/048242 International Preliminary Report on Patentability dated Nov. 10, 2016".
(Continued)

*Primary Examiner* — Majid Jamialahmadi
(74) *Attorney, Agent, or Firm* — Wilson Sonsini Goodrich & Rosati

(57) ABSTRACT

A catheter extraction tool has a head that can be placed in position to significantly surround a diameter of a catheter. The head is shaped to have a low enough profile above the catheter to allow the head to be slid down the catheter and into a subdermal region in which the catheter is subdermal with respect to a patient. The head of the catheter extraction tool is expanded sufficiently to slide the head over a catheter cuff located in the subdermal region. After the head of the catheter extraction tool slides over the catheter cuff, the head is contracted to engage the catheter so that a user can pull the catheter out of the patient using the catheter extraction tool.

14 Claims, 21 Drawing Sheets

Related U.S. Application Data continuation-in-part of application No. 14/846,989, filed on Sep. 7, 2015, now abandoned.

(60) Provisional application No. 62/209,216, filed on Aug. 24, 2015.

(51) Int. Cl.
   *A61B 17/28* (2006.01)
   *A61B 17/3205* (2006.01)
   *A61B 17/32* (2006.01)

(52) U.S. Cl.
   CPC ........ *A61M 25/00* (2013.01); *A61M 25/0017* (2013.01); *A61B 2017/320044* (2013.01); *A61B 2017/320056* (2013.01)

(56) References Cited

U.S. PATENT DOCUMENTS

| | | |
|---|---|---|
| 7,758,590 B2 | 7/2010 | Daniele et al. |
| 8,709,030 B1 | 4/2014 | Schleicher |
| 10,052,128 B2 | 8/2018 | Herscu et al. |
| 2007/0118148 A1 | 5/2007 | Daniele et al. |
| 2007/0185510 A1* | 8/2007 | Tran ................ A61B 17/00008 606/167 |
| 2007/0244490 A1 | 10/2007 | Moehle et al. |
| 2008/0195130 A1 | 8/2008 | Batiste |
| 2010/0024113 A1 | 2/2010 | Ge et al. |
| 2010/0049116 A1 | 2/2010 | Kerr |
| 2010/0241133 A1 | 9/2010 | Daniele et al. |
| 2012/0083815 A1* | 4/2012 | Troendle .......... A61B 17/32053 606/170 |
| 2012/0095475 A1 | 4/2012 | Barmada |
| 2012/0101513 A1* | 4/2012 | Shadeck ............ A61B 17/1659 606/170 |
| 2012/0203240 A1 | 8/2012 | Delahoussaye et al. |
| 2013/0282009 A1 | 10/2013 | Knodel |
| 2015/0080896 A1* | 3/2015 | To ...................... A61B 17/1671 606/79 |
| 2015/0257785 A1 | 9/2015 | Seitz |
| 2017/0056045 A1 | 3/2017 | Herscu et al. |
| 2017/0215855 A1 | 8/2017 | Nunan |

OTHER PUBLICATIONS

"PCT/US2016/048242 International Search Report dated Nov. 10, 2016".
"U.S. Appl. No. 14/846,989 Office Action dated Oct. 6, 2017".
"U.S. Appl. No. 15/011,341 Notice of Allowance dated Apr. 17, 2018".

* cited by examiner

CATHETER EXTRACTION

CROSS-REFERENCE TO RELATED APPLICATIONS

This application is a divisional of U.S. patent application Ser. No. 15/011,341, filed Jan. 29, 2016, now U.S. Pat. No. 10,052,128, which is a continuation-in-part of U.S. application Ser. No. 14/846,989, filed Sep. 7, 2015, which claims the benefit of U.S. Provisional No. 62/209,216, filed Aug. 24, 2015, the entire contents of which are incorporated herein by reference.

BACKGROUND OF THE INVENTION

1. Field of the Invention

The present invention relates generally to medical devices and methods. More particularly, the present invention relates to a removal and protocol for removing an implanted transcutaneous catheter, such as a tunneled central venous catheter.

A tunneled central venous catheter is a medical device which is placed with the tip of the catheter in the central venous system and which allows for administration of medication, for drawing blood for laboratory tests, for hemodialysis access, and the like. Such tunneled central venous catheters have an intravenous portion and a sub-dermal portion. The sub-dermal portion of has a catheter cuff or other fixation element that embeds into subcutaneous tissue to provide both an 'anchor" to hold the catheter in placer and a "seal" to inhibit the intrusion of bacteria and other contaminants. Such catheters are usually placed through the chest wall, tunneled under the skin, and enter the central venous system through the subclavian vein or internal jugular vein. The catheter tip is typically positioned in the superior vena cava or right atrium. Cuffed catheters can be also used for peritoneal dialysis and typically have both a subdermal cuff and a muscular cuff. Such cuffed peritoneal dialysis catheters may be inserted into the peritoneal cavity and used for long-term, ambulatory peritoneal dialysis.

Even though cuffed catheters are usually implanted for relatively long times, they are still temporary and must be removed when no longer needed. The presence of the cuff, however, complicates such removal. Almost instantly after catheter implantation, scar tissue, referred to as a sheath, begins to circumferentially form on the cuff and to a lesser extent on the catheter body. Cuffed catheters can remain implanted for months or even years, and the density and durability of the scar tissue increases over time exacerbating the removal difficulty.

Because of the scar tissue, catheter removal usually requires surgical dissection of the catheter and cuff from surrounding scar tissue followed by traction on the catheter for removal of the catheter and cuff. After removal, external pressure is applied to the catheter tract to stop bleeding. Such surgical removal procedures require skilled use of surgical instruments, such as an Iris scissor, a safety scalpel, and a curved hemostat. In difficult procedures, a counter-incision is needed for cuff access, and an incision may also be required at the exit site to widen the skin penetration. Once dissection is complete, the catheter is again pulled with gentle traction. These procedures are often performed in a clinic setting, an outpatient surgery center, or a hospital operating room depending on the patient's condition and the position of the catheter and cuff. Such removal procedures often require consultation with a surgical specialist, and the removal procedure may require 15 minutes or longer to complete including time to achieve hemostasis.

For these reason, improved devices, systems, methods, and protocols for removing implanted cuffed catheters are needed. In particular, it would be desirable if devices and methods were provided which increased the likelihood of successfully removing an implanted catheter without the need for a cut down or other surgical procedure, which reduced the time necessary for removing the catheter, and which decreased the trauma to the patient. At least some of these objectives will be met by the inventions described below.

2. Description of the Background Art

Previous cuffed catheter extraction catheters typically included a C-shaped shaft that was advanced over the catheter and used to dissect the cuff from surrounding tissue. The shaft was typically had a diameter larger than the cuff to allow the shaft to pass into and dissect the scar tissue surrounding the cuff. The shaft could include a serrated end to cut through peri-cuff scar tissue. An inner bead or blade was often rotated to cut the "fibrin sheath" away from the catheter, this allowing the catheter to be removed by traction on the catheter followed by application of pressure over the catheter tract for hemostasis. When used for inaccessible cuffs located far from the skin exit site, such prior extraction procedures often required additional cut-down when the scar sheath disruption was incomplete or when there was difficulty entering through the skin at the catheter exit site. Relevant patents and publications include: U.S. Pat. No. 7,758,590; US20070118148; US20070244490; US20080195130; and US20100241133 US20120203240.

SUMMARY OF THE INVENTION

The present invention provides a tool, typically a tissue dissection device, and a method for use of the tool in the removal or explantation of implanted, cuffed catheters of the type used for venous or hemodialysis access Although the tool is particularly suited for circumferential dissection of cuffed tunnel central venous and peritoneal dialysis catheters from scar tissue, the tools and methods of the present invention can be used for any form of tissue dissection in a variety of medical procedures.

In a first aspect, the present invention provides a tool for removing an implanted catheter having a catheter body and a cuff. The tool typically includes a removal head configured to immovably or fixedly secure to a distal end of an elongated manipulator. The removal head comprises a tubular body having an axial opening, such as a gap or slot, along one side to be placed over the catheter body. The tubular body usually has a blunt distal tip and first and second cutting edges extending obliquely in a proximal direction from the blunt distal tip. The blunt tip allows atraumatic insertion of the removal head over the body of the catheter and the cutting edges dissect scar and other tissue from both the catheter body and the cuff as the removal head is advanced distally using elongated manipulator.

In specific embodiments, the tool may further comprise cutting elements formed along the first and second cutting edges, where the cutting elements may be, for example, serrations. Alternatively, the cutting edges may be honed with a straight (non-serrated), be connected to en electro-surgical power supple to provide a cutting current, or the like. In all cases, first and second cutting edges will usually be swept back at an angle, generally but not necessarily from 30° to 60° relative to the perpendicular or radial direction. Optionally, the tubular body may have third and fourth cutting edges along opposed sides of the axial opening, where the third and fourth cutting edges are oriented to cut tissue as the removal head is rotated over the catheter body or cuff. Cutting elements, as described previously, may also be formed along the third and fourth cutting edges, or the third and fourth cutting edges may have any of the other forms described previously. Typically, the tubular body has a proximal face with an aperture which passes over the catheter body and cuff as the removal head is advanced distally. The aperture usually has cutting features over an interior peripheral edge, and the removal head body is typically tapered in the proximal direction so that the aperture has an area smaller than the cross-sectional area of distal regions of an interior volume of the removal head. In specific embodiments, the aperture has an oblong periphery.

Further specific embodiments of the tools of the present invention will further comprise the elongated manipulator, where the elongated manipulator usually comprises a shaft and a handle. The removal head may but is not necessarily integrally formed with the shaft, and the shaft often has an axial channel configured to receive the catheter body as the removal head is advanced over the catheter body. In particular embodiments, the shaft comprises a stem which removably attaches to the handle.

In a second aspect, the present invention provides a method for extracting an implanted cuffed catheter from a patient. The method comprises advancing a removal head over a body region of the catheter until a distal end of the removal head reaches a proximal end of the cuff. The removal head is further advanced so that the removal head passes over and encompasses the cuff. The removal head is then manipulated to dissect the cuff from surrounding tissue. The removal head is then further advanced over the catheter so that a proximal end of the removal head lies beyond a distal end of the cuff. At this point, the catheter body and the cuff are largely or completely dissected from the surrounded scar and other tissue, and the removal head can be retracted so that the proximal end of the removal head engages the distal end of the cuff to apply an extractive force against the cuff. By proximally drawing on the catheter body while retracting the removal head, the catheter and cuff can be extracted as a single piece.

In specific embodiments, the An atraumatic or other tip on the removal head is advanced through an insertion site of the catheter on the patient's skin. Once inserted over a proximal portion of the catheter body, the removal head is advanced over the body region and/or the cuff of the catheter to dissect tissue from said body region and/or the cuff. The removal head typically includes first and second cutting edges extending obliquely in a proximal direction from the tip so that the cutting edges dissect the tissue as the removal head is advanced. The removal head may also be rotated over the body region and/or the cuff of the catheter to further dissect tissue therefrom. The removal head usually further includes third and fourth cutting edges along an axial opening along one side thereof, and the axial opening is typically configured to allow the removal head to be placed over the body region of the catheter. A proximal end of the removal head has an aperture with a periphery that partially encircles the body region of the catheter as the removal head is advanced. The periphery of the aperture often has cutting features which dissect tissue as the removal head is advanced. The aperture typically has a width which is smaller than a width of the cuff so that the aperture compresses the cuff as the removal head passes over the cuff to further dissect tissue from the cuff.

BRIEF DESCRIPTION OF THE DRAWINGS

FIGS. 17A-1, 17A-2 and 17B-17D show different views of a further embodiment of the device having a serrated removal head.

DETAILED DESCRIPTION OF THE INVENTION

Efficient and expeditious extraction of a cuffed or other catheter is described herein. Since a cuff on the catheter is the most common type anchor and/or barrier on an implantable or long-term dwelling catheter, the term "cuff" will be used to denote any type of anchor, fixation, seal or other implantable feature on a catheter which can act to anchor or seal the catheter and which can become embedded in the tissue over time making the catheter difficult to extract. While, specific embodiments pertain to a tunneled central venous catheter, other types of catheters may be extracted as described herein, including catheters with alternative tunneling or fixation modalities.

The present invention is directed at a catheter extraction device and protocol that allows removal of a cuffed tunneled or other catheter in less time than existing methods with a reduced need for surgical skill. The catheter extraction device is advanced along the existing catheter until it meets the catheter cuff. The device then passes over the catheter cuff and is used to dissect the catheter cuff away from surrounding tissue. Once past the catheter cuff the device is used to break the sheath of scar tissue surrounding the catheter cuff to separate the catheter from any bodily attachment. Then the catheter extraction device is used to remove the catheter with gentle traction force.

The catheter extraction device and method described herein facilitates removal of catheters by non-surgeons in a hospital or office setting without consultation to a specialist. This provides for less delay in catheter removal as well. It is a less painful procedure for the patient and decreases trauma to the surrounding tissues. In addition, catheter removal procedure time is decreased.

For example, a catheter extraction device is produced in either disposable or reusable forms and is made available to doctor offices and hospitals as an "off the shelf" solution when tunneled catheter removal is necessary.

Figure 1:
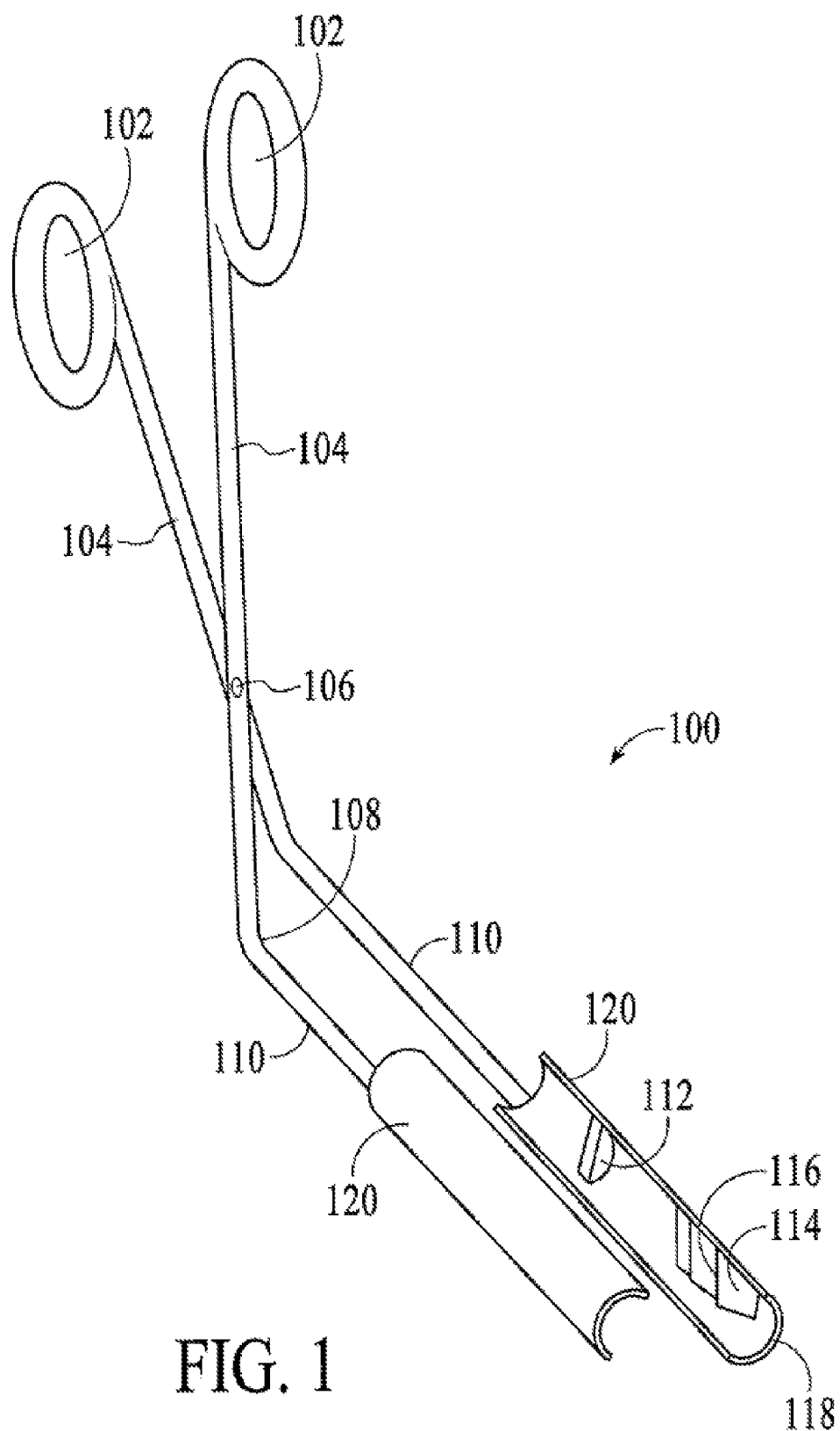
FIG. 1 is an angled front view of a catheter extraction device in accordance with an implementation.

FIG. 1 shows a catheter extraction device 100 that can be opened and closed using the opposing fingers by inserting the opposing fingers into finger holes 102 within a handle of catheter extraction device 100. For example, catheter extraction device 100 also includes pre-joint shafts 104, a joint 106, and post-joint shafts 110. Each post-joint shaft 110 has, for example, a bend 108 at an angle of approximately 15 degrees. Alternatively, for bend 108 any angle from 0 to 179 degrees may be utilized depending upon a specific application.

A head of catheter extraction device 100 includes, for example, curved body parts 120 that, when fully closed, fits around a catheter. Each curved body part 120 has, for example, an angled platform 114 on which lies a sharp edge 116. A distal edge 118 of each curved body part 120 is, for example, rounded such that it contours to the catheter and does not cut or damage skin and other tissues. Alternatively, other shapes can be used for distal edge 118. For example, the exact shape of distal edge 118 can be squared, spherical or any other shape that can improve performance. In alternative implementations in addition to the implementation shown in FIGS. 1 and 2, a convex curved head element can be replaced with a locking gear mechanism that can be manipulated through rotation of the handle. Other variations of a blade with catheter cuff grip facility also can be used to facilitate extracting a tunneled central venous catheter.

For example, catheter extraction device 100 is mounted on an existing catheter and advanced through the defect in the skin, where the catheter exits the patient. This is done, for example, by surrounding the catheter with curved body parts 120 of catheter extraction device 100 near the catheter exit site. Curved body parts 120 compress the catheter slightly to allow for a low profile allowing advancement of the head of catheter extraction device 100 through the existing catheter exit site. Then, curved body parts 120 are slid along the catheter (distal edge 118 of the head first) using moderate pressure until distal edge 118 of the head reaches the catheter cuff. The length of post-joint shaft 110 is, for example, long enough to reach past the catheter cuff on any tunneled central venous catheter.

At this point curved body parts 120 are expanded (i.e., the head is opened) in order to dissect the catheter cuff from surrounding tissue and in order to allow for enough room for curved body parts 120 to slide past the catheter cuff. Then, slight pressure is given to the catheter extraction device 100 to push curved body parts 120 past the catheter cuff. Once the angled platform 114 and sharp edge 116 of curved body parts 120 pass the catheter cuff, the catheter extraction device 100 is squeezed lightly and inserted until a backstop 112 on each of curved body parts 120 comes in contact with the catheter cuff. The user squeezes the handle of catheter extraction device 100 so that sharp edges 116 cut any remaining sheath of scar tissue that prevents the catheter from freely sliding out of the patient. The user then firmly squeezes the handle of catheter extraction device 100 and pulls to remove the catheter in its entirety.

Figure 2:
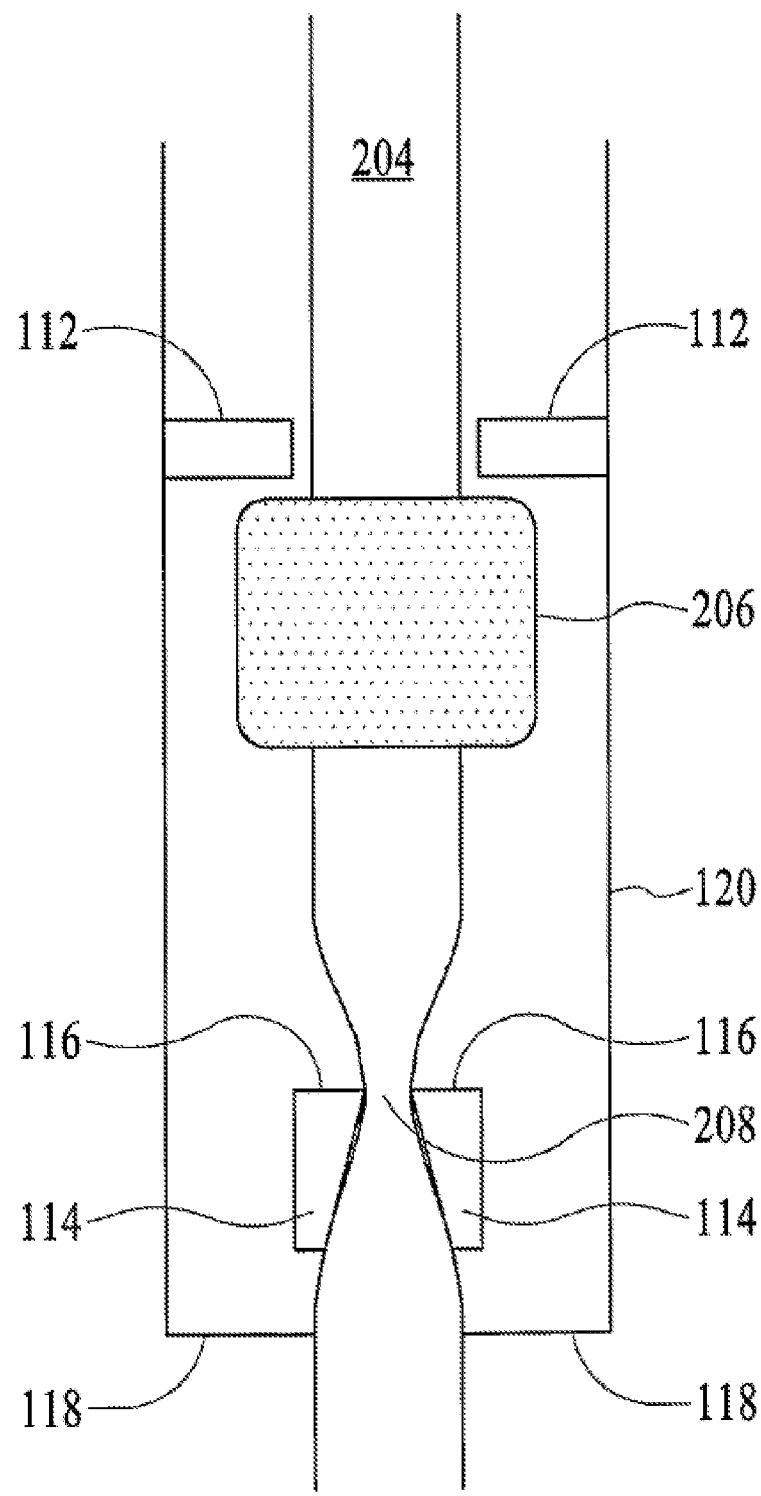
FIG. 2 is an enlarged front view of a head of the catheter extraction device shown in FIG. 1 clamped around a catheter just distal to a catheter cuff in accordance with an implementation.

FIG. 2 illustrates an enlarged front view of catheter extraction device 100 as it lies in a clasped position past a catheter cuff 206. The backstop 112 on each of curved body parts 120 should preferably rest up against a distal edge of catheter cuff 206, and the curved body should surround a pre-cuff catheter portion 204. As the catheter extraction device 100 is squeezed, angled platform 114 and sharp edge 116, compress a post-cuff catheter portion 208 and preferably also cut through any sheath that may have formed bound to post-cuff catheter portion 208.

Figure 3:
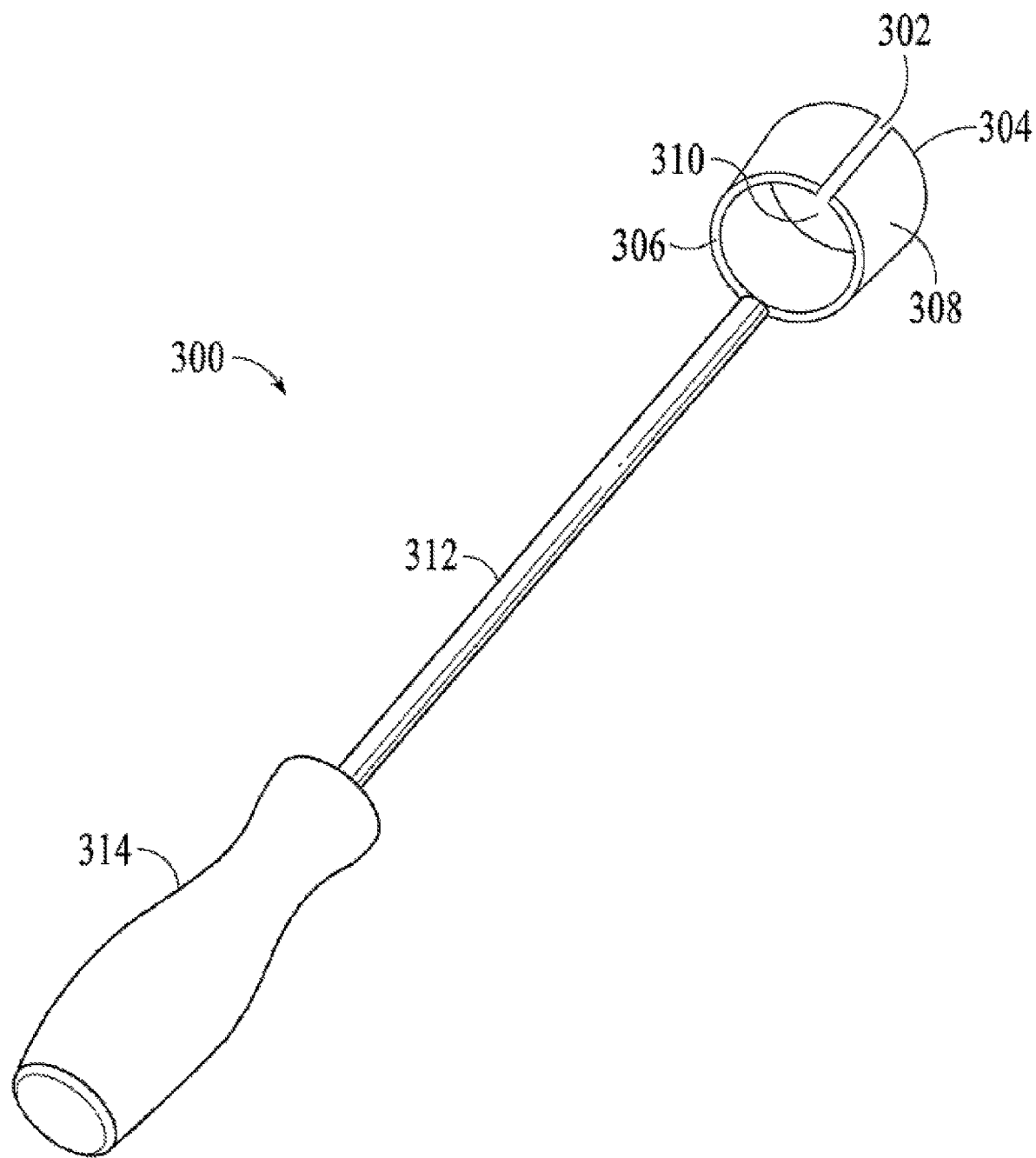
FIG. 3 is an angled view of a catheter extraction device in accordance with another implementation.

FIG. 3 illustrates another implementation of a catheter extraction device. Catheter extraction device 300 includes a gripping handle 314, a shaft 312, and a cylindrical head composed of a curved body 308 with an opening 302. Curved body 308 surrounds a space 310 into which is placed catheter that is to be extracted. Curved body 308 includes a proximal beveled bladed edge 306 with an approximate circumference of that of the catheter, and a non-sharp distal edge 304 with a slightly larger circumference to accommodate the cuff. For example, curved body 308 is composed of spring steel. Alternatively, other materials can be used such as stainless steel, a polymer plastic, carbon based such as carbon fiber, embedded plastic with metal, autoclave plastic, or some other suitable material.

To extract a catheter from a patient, the catheter is squeezed into opening 302 to load the catheter into space 310. Catheter extraction device 300 is then slid along the catheter through an epidermal opening of the patient until the non-sharp distal edge 304 reaches the catheter cuff.

With pressure, the spring steel of curved body 308 opens at the catheter cuff allowing curved body 308 to pass the catheter cuff and begin dissection of any surrounding tissue from the catheter cuff using non-sharp distal edge 304. Once past the catheter cuff, the spring steel of curved body reverts to its original shape and this force, coupled with a small amount of rotation, allows for beveled bladed proximal edge 306 to engage the subcutaneous sheath, subdermal scar, or any other material, at the catheter cuff and dissect it away from the catheter. Once this tissue has been dissected from any catheter elements, a gentle traction force can be applied to Catheter extraction device 300, removing the catheter from the patient.

Figure 4:
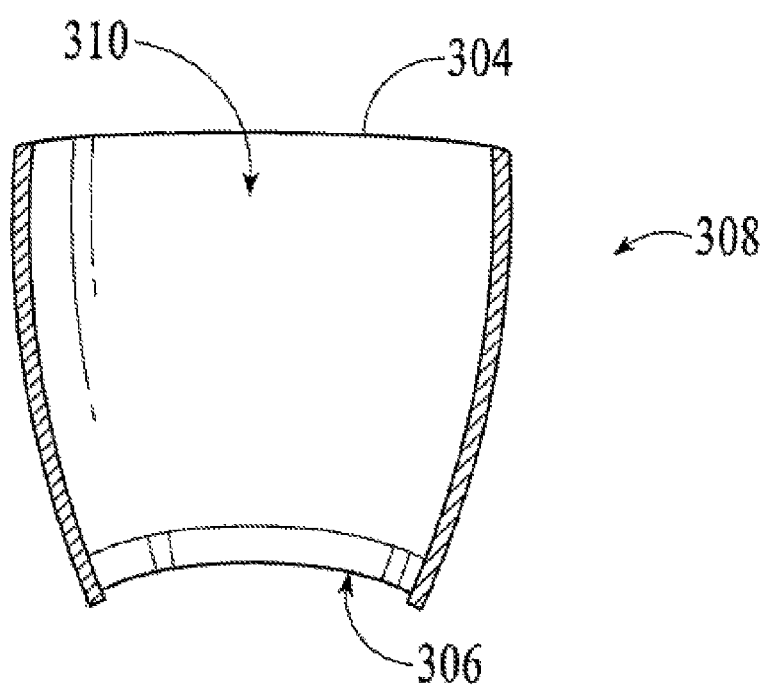
FIG. 4 is an enlarged view of a sectional view of a head of the catheter extraction device shown in FIG. 3 in accordance with another implementation.

FIG. 4 illustrates an enlarged view of a cross section of the preferred embodiment of the distal circular head in FIG. 3. Curved body 308 surrounds space 310 which has a diameter approximately equal to that of the catheter that is to be removed at the proximal end. Non-sharp distal edge 304 is used to dissect the surrounding tissue as the spring steel of curved body 308 expands around the catheter cuff. The beveled blade proximal edge 306 engages the "sheath" at the catheter cuff and breaks it. In this example, a simple conical body with beveled blade proximal edge is used. However, any conical body, such as a conical inverted j-shape or any other conical shape can be used. These different body shapes can have singular or multiple blades affixed to their edges. In some instances, the body can further have internal diameter variance. This variance allows for optimizing the capturing of surrounding tissue for dissection.

Figure 5A:
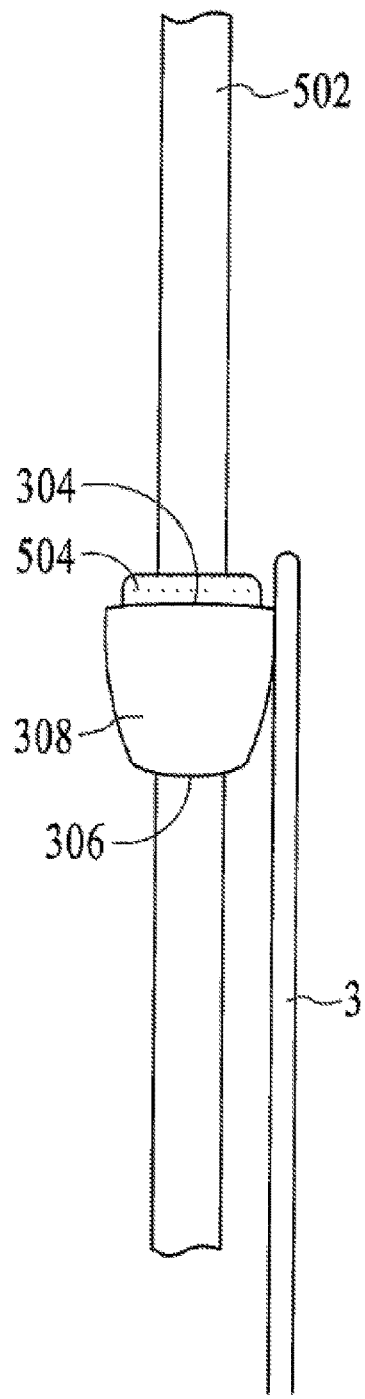
FIG. 5A, FIG. 5B and FIG. 5C show the catheter extraction device shown in FIG. 3 moved over a catheter cuff in accordance with an implementation.
Figure 5B:
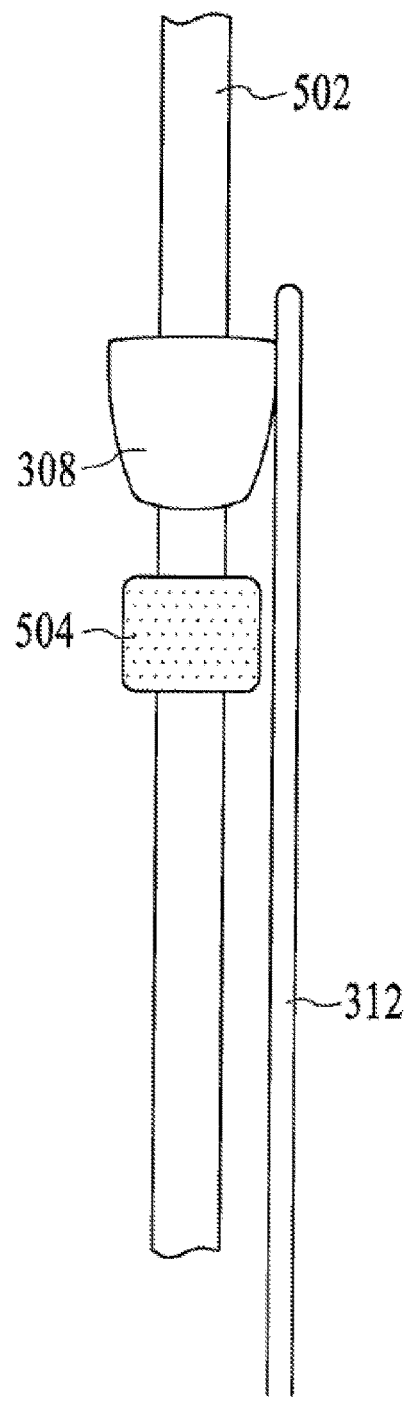
Figure 5C:
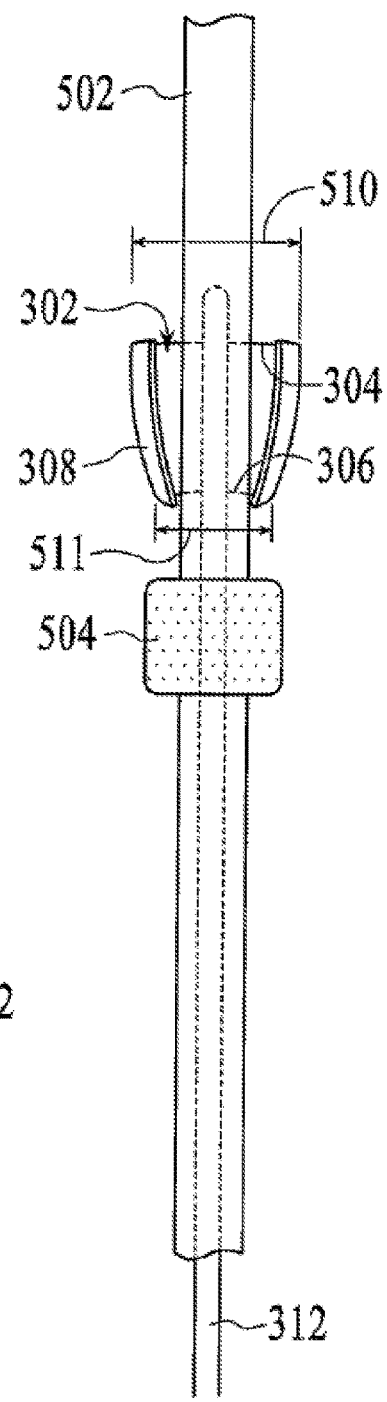

FIG. 5A and FIG. 5B illustrate how curved body 308 attached to the rod 312 moves over and past catheter cuff 504 on catheter 502. As the larger and distal edge 304 of curved body 308 hits catheter cuff 504, space 302 between within two parts of curved body 308 widens allowing for proximal edge 306 to pass over the catheter cuff 504. FIG. 5C illustrates how when rod 312 is used to withdraw catheter extraction device 300, diameter 511 of beveled blade proximal edge 306 is reduced relative to diameter 510 of beveled blade proximal edge 306 allowing curved body 308 to engage catheter cuff 504 and pull catheter 502 out from the patient.

Figure 6:
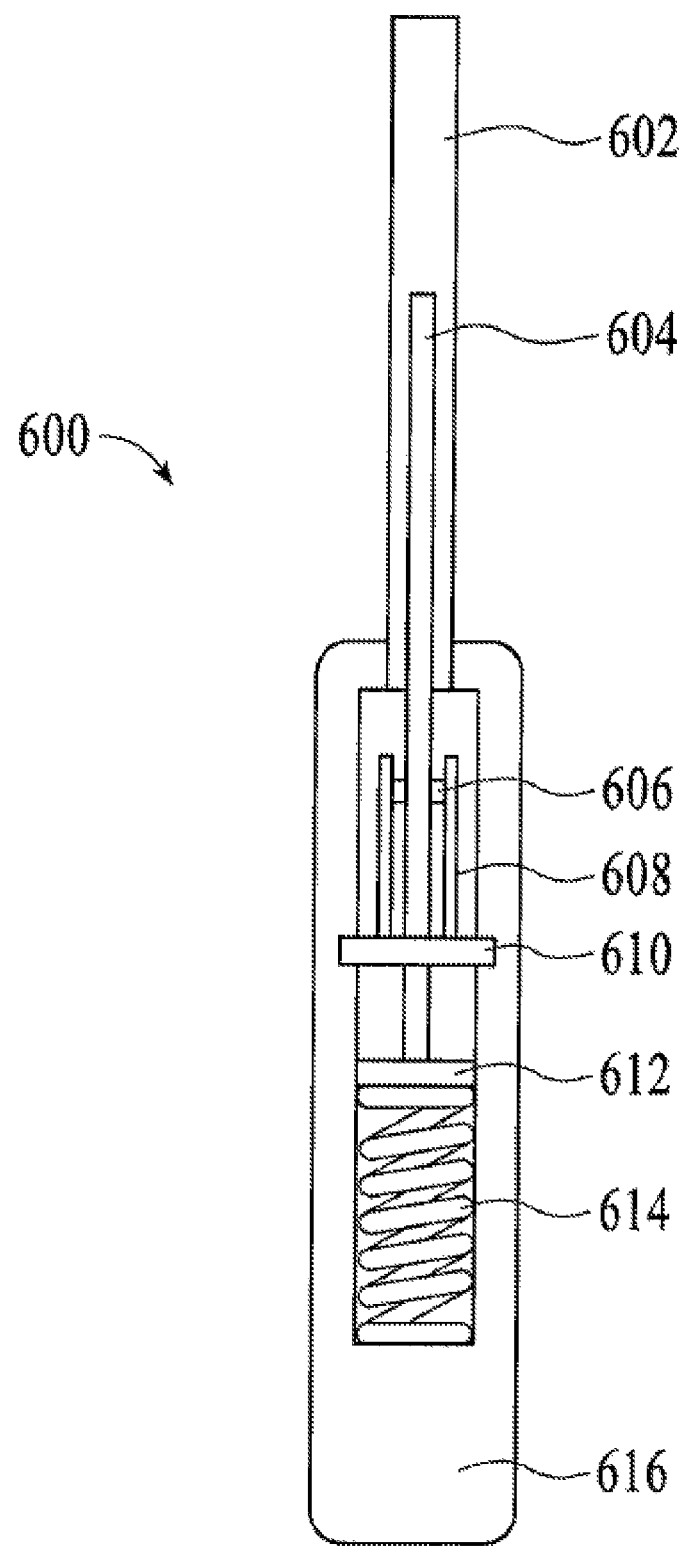
FIG. 6 shows the handle of a catheter extraction device that allows for a rod or wire to be manipulated in order to change a form of a distal head in accordance with another implementation.

FIG. 6 illustrates another implementation of a catheter extraction device. Catheter extraction device handle portion 600 includes a handle 616 and a shaft 602 for a rod 604. Rod 604 has a base 612 and a small bar 606, which is attached to a large bar 610 using a flat connector 608. A spring 614 is located within handle 616.

Figure 7A:
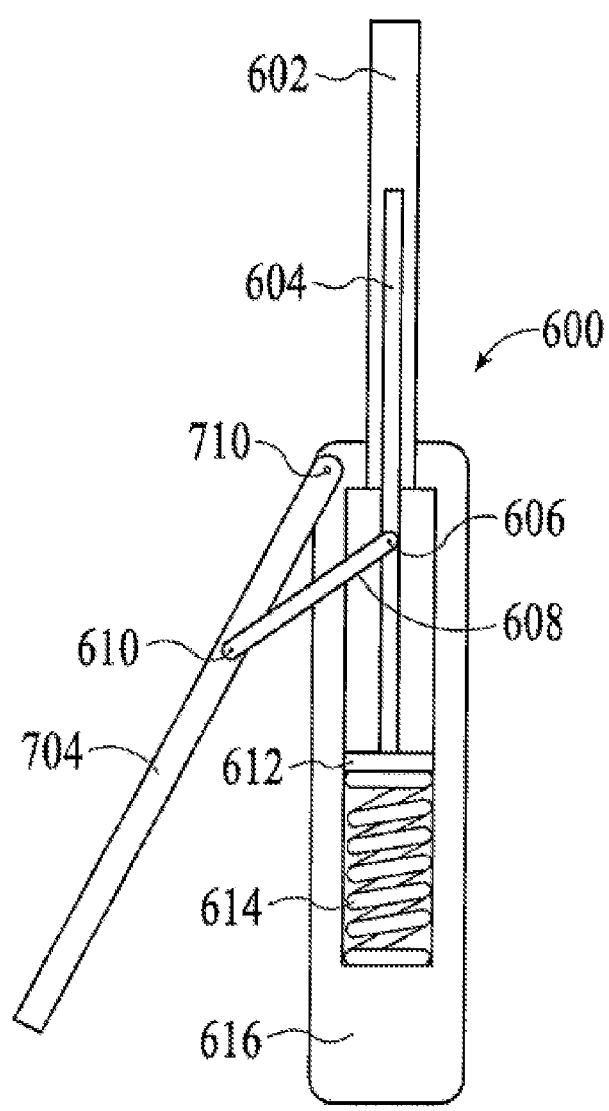
FIG. 7A is a side view of the handle of a catheter extraction device shown in FIG. 6 in accordance with an implementation.

As shown in FIG. 7A, a lever 704 has been attached to handle 616 at a joint 710. Lever 704 is connected to flat connector 608 at large bar 610. The location of small bar 606 is also shown in FIG. 7A. Note that in this example 606 and 610 are bars but joints can also be used. Force can be applied to lever 704 in order to rotate lever 704 at joint 710 and bring lever 704 closer to handle 616. This force and movement of lever 704 preferably manipulates large bar 610 which will then in turn manipulate small bar 606 as small bar 606 is connected with flat connector 608. This action preferably moves rod 604 down shaft 602 to open an attached head on a distal end. Spring 614 attached to the base 612 is preferably extended during this action as well. Once force is removed from lever 704 attached to handle 616, spring 614 preferably recoils causing the rod 604 to return to its original position by sliding back down shaft 602. In this example, a lever with spring system is used to actuate the system. However, in some instances, a ratcheted mechanism can perform the same task. A ratchet system differs slightly in that actuation moves the rod an incremental amount forward, opening the head. Successive ratchet movements further the rod down the shaft until such time the user has opened the head to its widest diameter. When set in reverse, ratchet movements move the rod back down the shaft and closes the head.

Figure 7B:
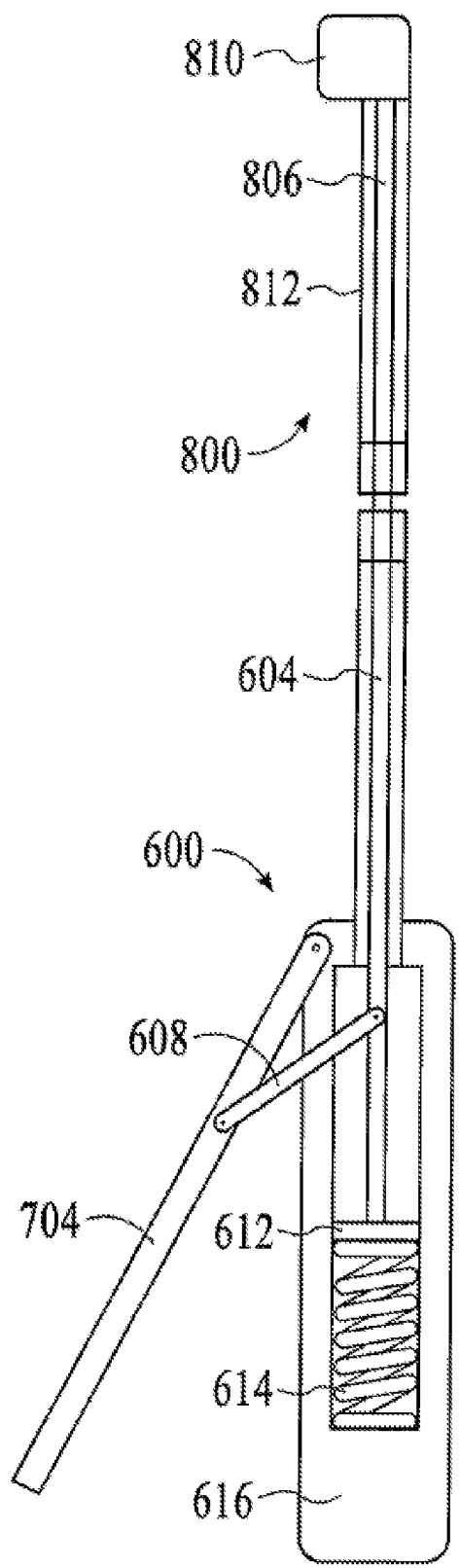
FIG. 7B shows a head portion added to the handle of a catheter extraction device shown in FIG. 7A in accordance with an implementation.

FIG. 7B illustrates how catheter extraction device head attachment 800 attachment can be fitted onto catheter extraction device handle portion 600. Rod 806 in catheter extraction device heat attachment 800 can be manipulated by rod 604 of catheter extraction device handle portion 600 and causes a head 810 attached to a shaft 812 to open allowing for head 810 to pass over a catheter cuff on a catheter.

Figure 8:
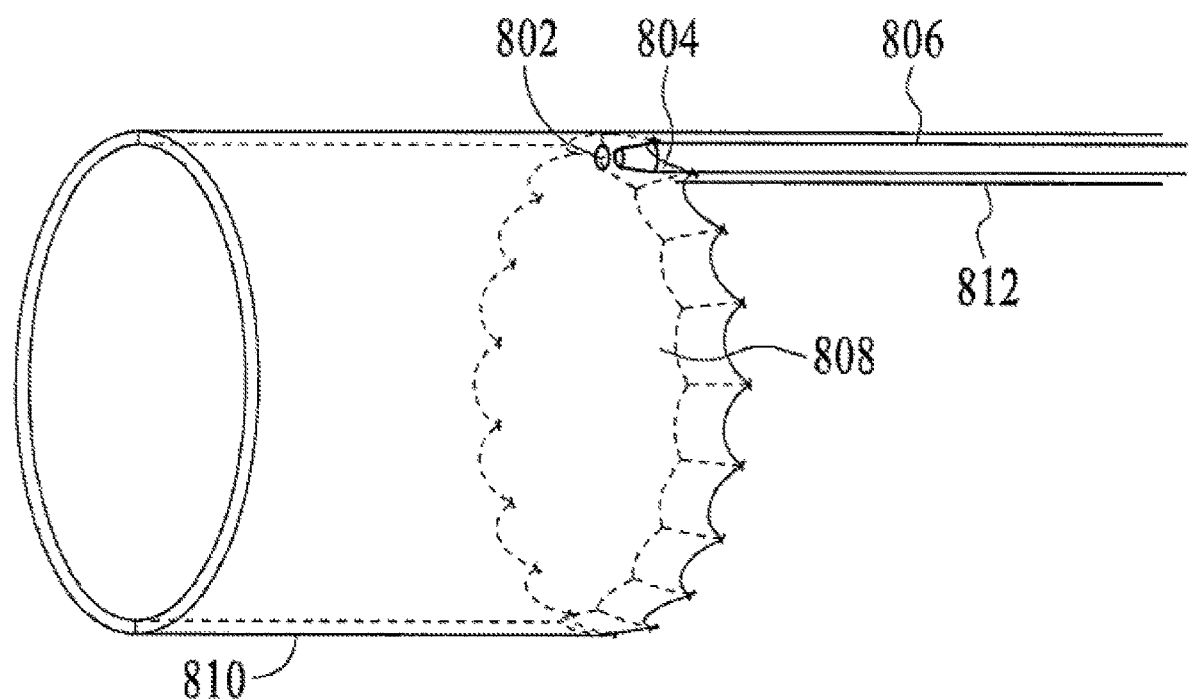
FIG. 8 is an enlarged side view of a head of the catheter extraction device shown in FIG. 7B in accordance with an implementation.

FIG. 8 illustrates how a tip 804 of rod 806 enters into a slot 802 on head 810, which then widens a space 808 allowing for head 810 to pass over the catheter cuff.

Figure 9A:
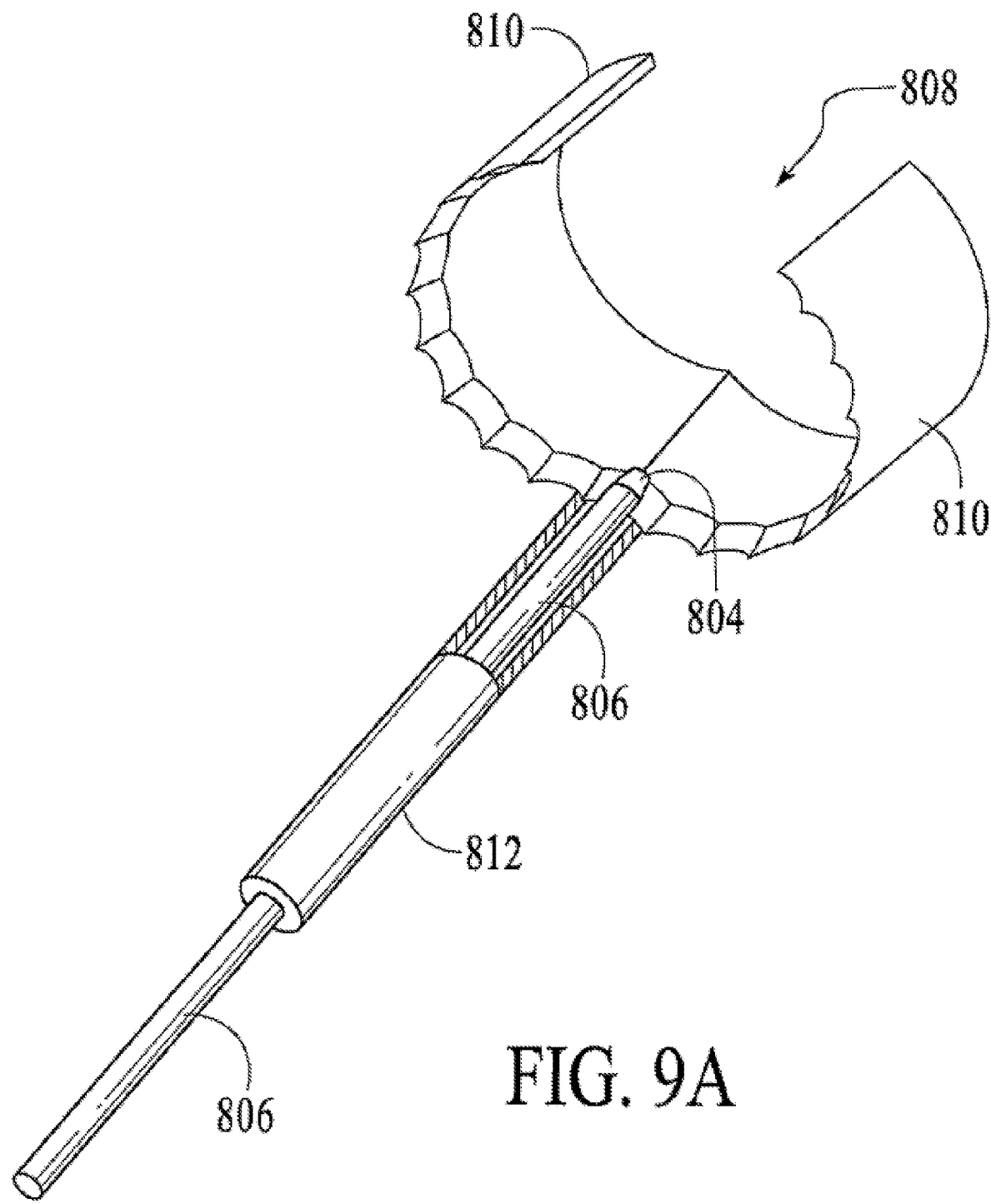
FIG. 9A and FIG. 9B present enlarged angled views illustrating the opening of the head of the catheter extraction device shown in FIG. 7B in accordance with an implementation.
Figure 9B:
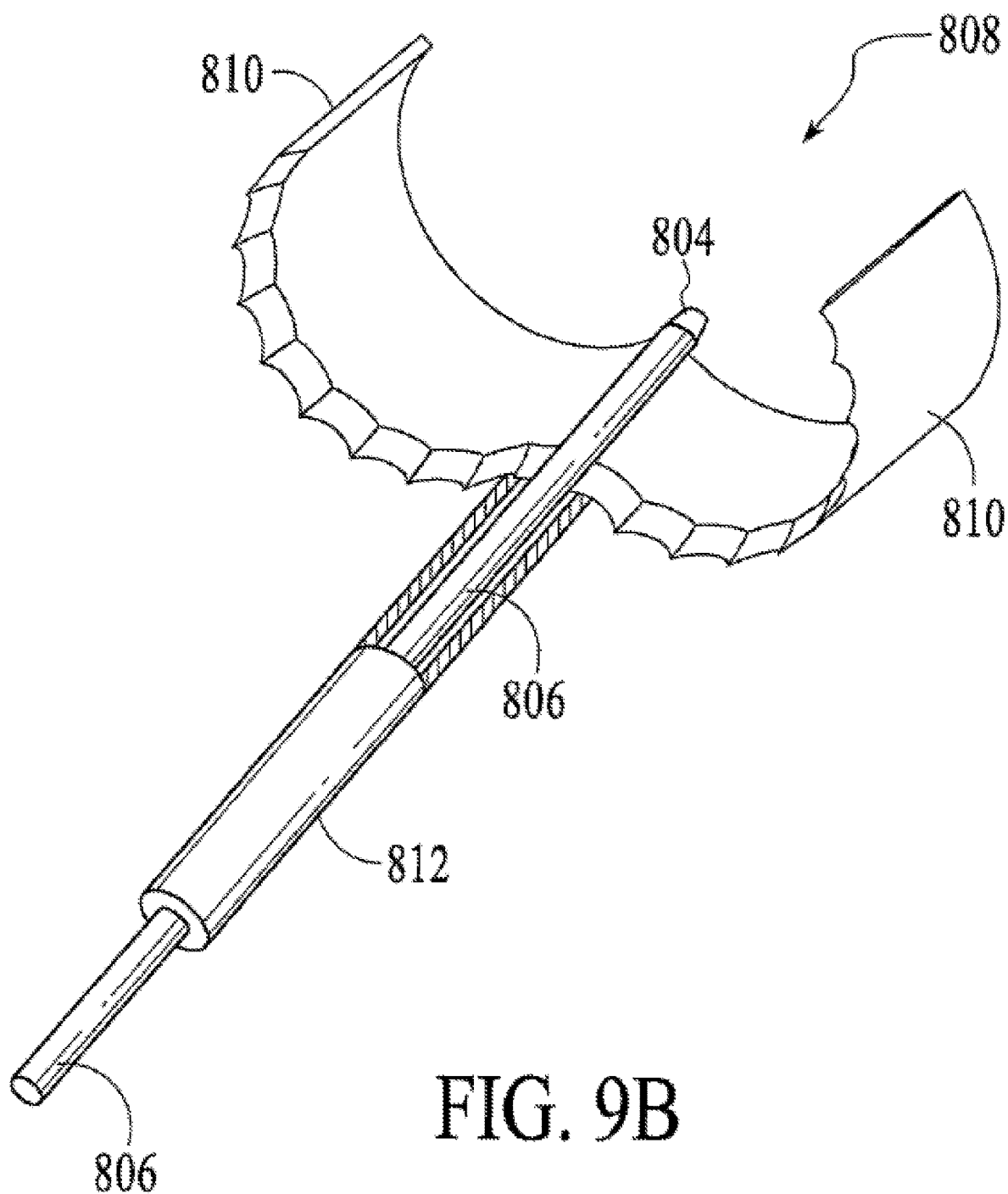

FIG. 9A and FIG. 9B illustrate an enlarged cut-out view that illustrates the dynamics of the opening of head 810. As rod 806 is pushed down the shaft 812, tip 804 preferably pushes at the bases of the left piece of head 810 and the right piece of head 810 surrounding space 808. Upon further force, pieces of head 810 preferably widen in angle and increasing space 808 which will allow for head 810 to dissect any tissue from the catheter cuff and pass over it.

Figure 10:
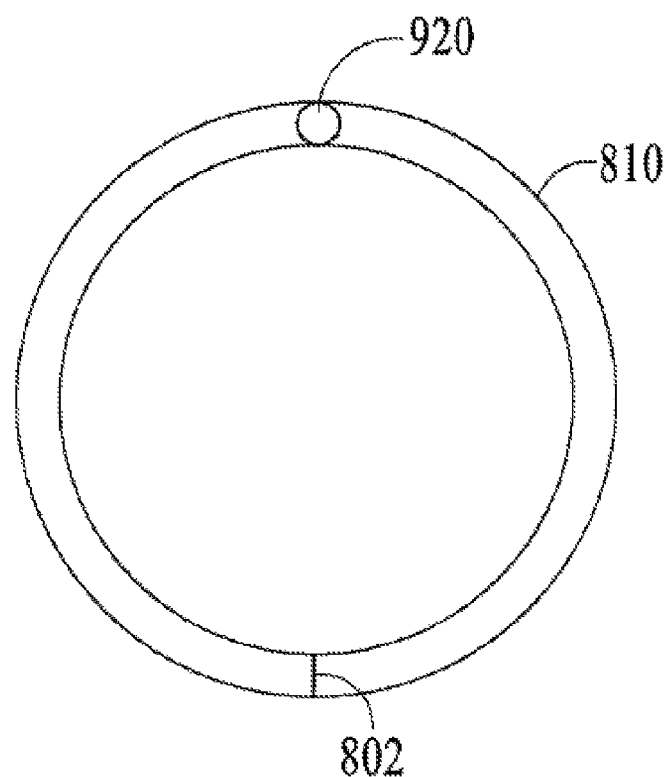
FIG. 10 and FIG. 11 illustrate operation of the of the head of the catheter extraction device shown in FIG. 7B in accordance with an implementation.
Figure 11:
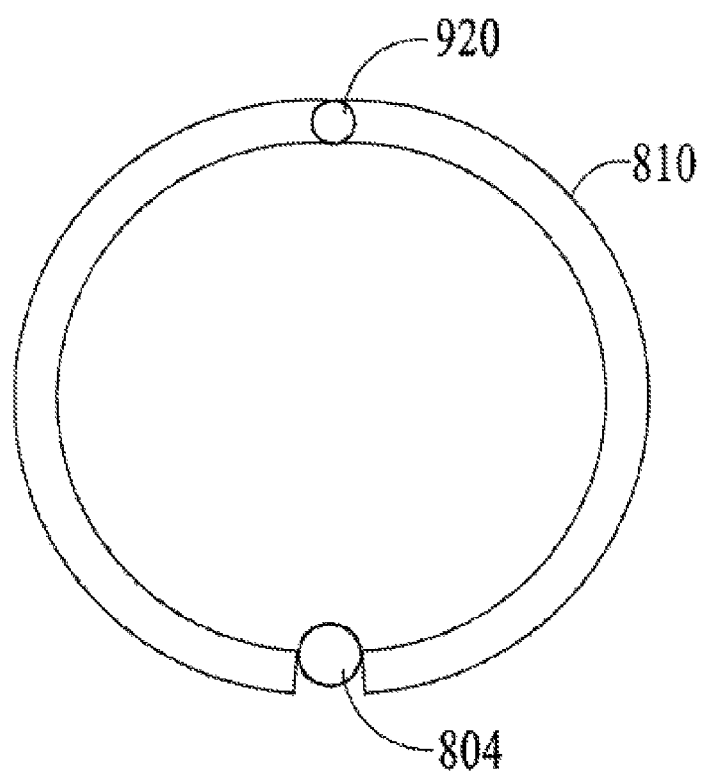

FIG. 10 and FIG. 11 further illustrate operation of head 810. Head 810 employs a catheter gripping facility with subdermal scar cutting capability. Head 810 is composed of two cylindania connected by a pivot pin with an embedded torsion spring 920. In its normal state, the torsion spring applies torque that continuously forces both cylindania at a torque axis point to form a closed cylinder as illustrated by FIG. 10.

To open head 810, a user actuates lever 704 to move a rounded end tip 804 of rod 806 so that rounded end tip 804 meets a notched opening 802 of head 810. As shown by FIG. 11, as rounded end tip 804 of rod 806 continues to be moved towards and through head 810, the cylindania of head 810 open to allow room for rod 806 to pass through.

For example, a user can continue to actuate lever 704 until head 810 opens a desired amount, for example, approximately 3 millimeters. In this example, 3 millimeters has been used, but any distance that sufficiently allows head 810 to pass the catheter cuff can be used. Once head 810 passes the catheter cuff, the user will release grip on lever 704 to reverse, allowing rod 806 to be withdrawn from head 810 so that embedded torsion spring 920 will cause the cylindania of head 810 to revert back to the closed position shown in FIG. 10. At this point, subdermal scar adhering to any catheter elements may prevent removal of the catheter from the patient.

Figure 13:
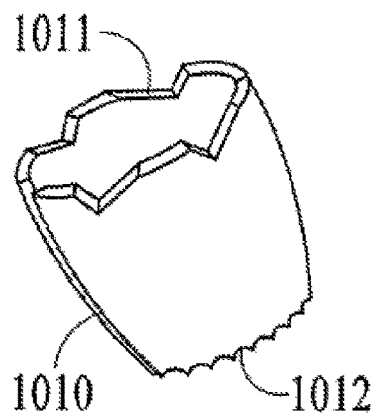

For example, head 810 is shaped similar to a head 1010 shown in FIG. 13. To remove subdermal scar adhering to any catheter elements, the proximal edge of head 810 contains within an inner diameter a serrated edge (similar to a serrated edge 1012 shown in FIG. 13). While a user manipulates handle 616 using any combination of pulling, pushing and or rotating motions, any adherent scar will be cut away from the catheter. In addition, the distal edge of head 810 can use an angled or beveled serrated edge (similar to a serrated edge 1011 shown in FIG. 13) for further tissue dissection while traversing towards catheter cuff 504 using the same motions. Once the catheter is freed from the scar tissues, the user will be able to extract the catheter from the patient.

In the above example implementations, a symmetrical cylindrical head is depicted but any shape that improves performance is also disclosed. In all cases, exterior surfaces are smooth and rounded.

Also, the rod system shown in FIGS. 6 through 11 may be interchanged with a wire system that allows for the same purpose of opening the head of a catheter extraction device. The spring mechanism shown in FIGS. 6 through 11 can also be interchanged with any other mechanism, such as a ratcheted system, used to bring the catheter extraction device 100 back to its original position after force has been removed from a lever.

Also, catheter line diameters may vary based on application. Dimensions of the heads of the catheter extractions devices described above can be varied to fit any tunneled central venous catheter implementations.

Figure 12:
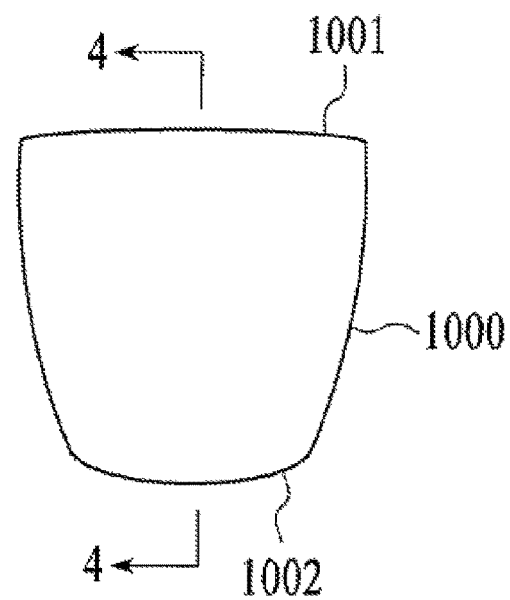
FIG. 12, FIG. 13, FIG. 14 and FIG. 15 show various alternative implementations of head shapes for a catheter extraction device.

FIG. 12, FIG. 13, FIG. 14, and FIG. 15 show various alternative implementations of head shapes for a catheter extraction device. FIG. 12 illustrates that a diameter at an edge 1001 of a head 1000 is larger than a diameter at an edge 1002. After edge 1001 is pushed over a catheter cuff, head 1000 expands so that edge 1002 also travels over the catheter cuff before head 1000 contracts allowing edge 1002 to engage with the catheter cuff.

FIG. 13 shows edge 1011 of head 1010 being a serrated cutting edge to allow for the head to separate the catheter and the catheter cuff from any bodily attachment. Edge 1012 can also be serrated. Serrated or sharpened edges may be placed on any surfaces of the heads shown in FIGS. 12, 13, 14 to produce cutting edges that provide cutting ability to dissect the cuff from the tissue and/or cut the scar sheath to remove the catheter.

Figure 14:
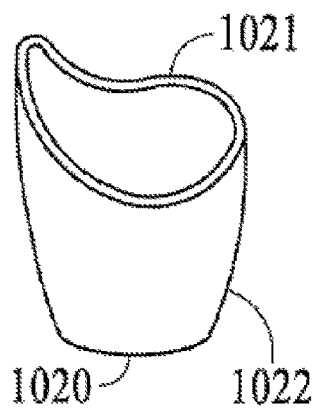
Figure 15:
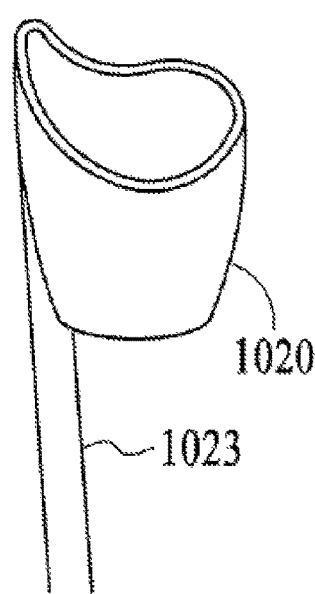

FIG. 14 shows an edge 1021 of a head 1010 being a cutting edge to allow for the head to separate the catheter and the catheter cuff from any bodily attachment. Edge 1022 can also be serrated. FIG. 15 shows a shaft 1023 connected to head 1020.

Figure 16A:
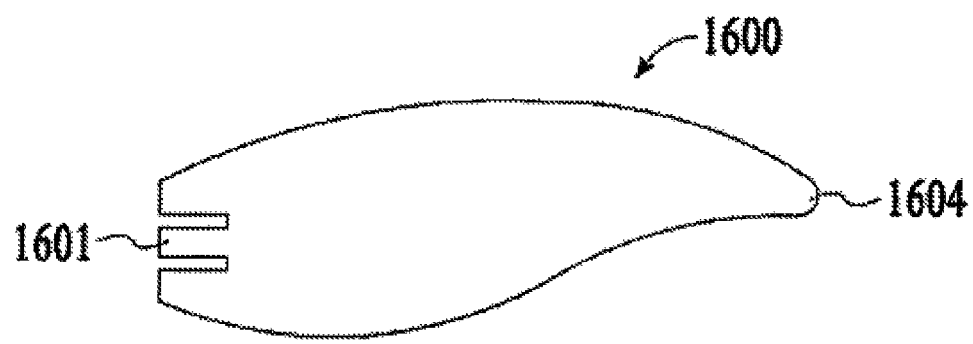
FIG. 16A, FIG. 16B and FIG. 16C each show an alternative head geometry for the catheter extraction device of the present invention.
Figure 16B:
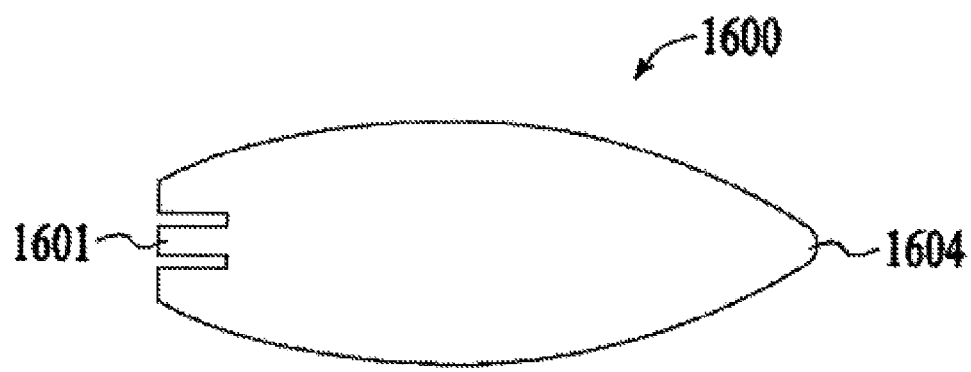
Figure 16C:
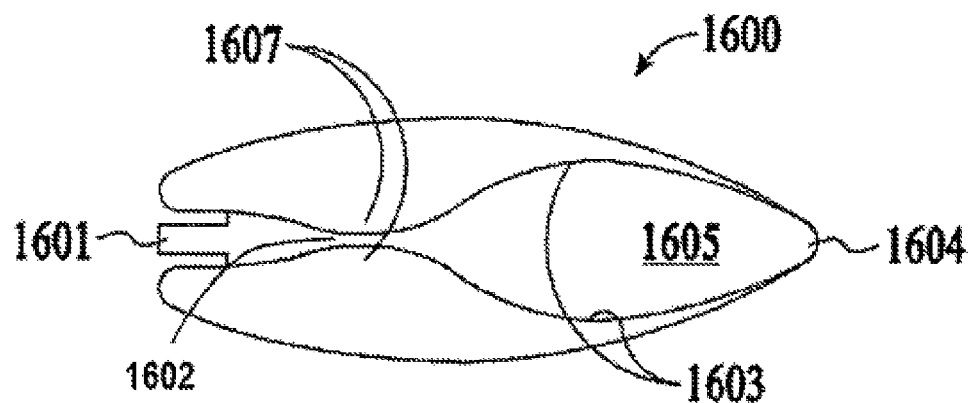

FIG. 16A, FIG. 16B and FIG. 16C show various views of another preferred embodiment of a head 1600. Head 1600 consists of a preferably pointed tip 1604, cutting edges 1603 that line distal ends of wings 1607, which surround a space 1605. Preferably included is also a catheter insertion point 1602 and flexible end pieces 1601. The catheter is preferably inserted at the catheter insertion point 1602 until surrounded by wings 1607, and able to move through space 1605. Using a shaft, head 1600 is preferably pushed along the catheter and past the dermal entry until it reaches the cuff on the catheter. Wings 1607 hold the catheter securely within during the motion.

Once head 1600 is subdermal, it is preferably guided by the shaft until it hits the catheter cuff. At this point, pointed tip 1604 is used to penetrate the tissue surrounding the catheter cuff and pass it. Most likely, the ratcheted system would be used to move head 1600 in a controlled manner past the cuff but any system could be used. For example, an axial rotation and twisting motion can be used while continually exerting forward force. Cutting edges 1603 are preferably used to cut most of or all of the tissue surrounding the catheter cuff. Wings 1607 can be rigid or slightly flexible and open slightly as they pass over the cuff. The flexible end pieces 1601 preferably widen allowing the entirety of head 1600 to pass over the catheter cuff. Once past the catheter cuff, flexible end pieces 1601 narrow again and put pressure inwards onto the scar sheath surrounding the catheter past the catheter cuff. The user can then pull back on the shaft and device which allows for the flexible end pieces 1601 to grip and cut some or all of the scar sheath allowing for the catheter to be removed using traction. During the pulling force, head 1600 and/or the flexible end pieces 1601 can also preferably evert allowing for a more perpendicular cutting force to be applied to the scar sheath surrounding the catheter.

A motorized version of the catheter extraction tool can be used where the head is connected to a rotating or oscillating motor element. This can allow for more effective dissection of tissues during cuff dissection or scar sheath division.

FIGS. 17A-1, 17A-2 and 17B-17D shows a further embodiment of the present invention comprising a device 1700 having a removal head 1702 attached to or formed integrally with a distal end of a shaft 1704. A handle 1706 is removably attached to a proximal end of the shaft, typically via a male stem 1708 which can be inserted into a suitable receptacle in a distal end of the handle 1706. The removal head 1702 and shaft 1704 may be disposable while the handle 1706 may be sterilizable and reusable. The shaft 1704 is shown as a linear element but may alternatively be curvilinear to accommodate catheters that follow a curvilinear path through the subdermal tissues. The shaft will usually have an axial groove or channel 1710 formed over most or all of its length, and the groove or channel will usually extend through and be contiguous with a passage or channel 1712 in the removal head as described in more detail below. Preferred construction materials for the cutting head and the shaft material include stainless steels and/or a hard, sterilizable plastic materials, but other materials might also find use.

A quick release button 1707 may be provided at the proximal end of the handle 1706 but can be situated anywhere on the handle. The device may alternatively have a monolithic design where the removal head 1702, the shaft 1704, and the handle 1706 are formed as a single integrated unit which may be disposable or sterilizable, typically being autoclavable. The design of the removal head 1702 allows the device 1700 to dilate the skin exit site of the catheter with a minimal incision or no incision and allows for removal of the catheter without any other surgical instrument. The removal head 1702 cuts tissue both when advancing and retracting the device and allows optional rotation of the device to facilitate cutting when both advancing and retracting. The device may be used for removal of all cuffed catheters including central venous and peritoneal catheters.

Figures 1, 17A:
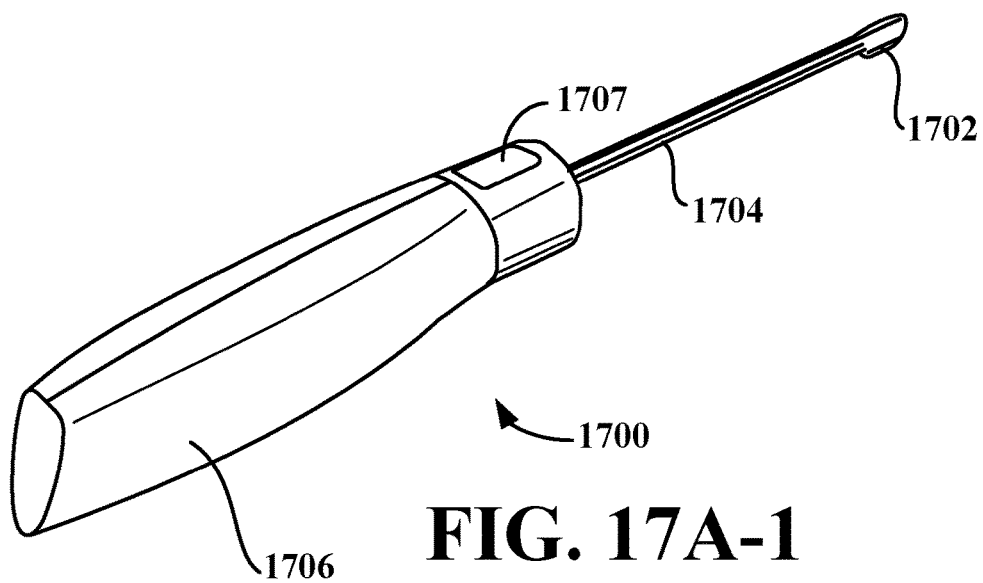
Figures 2, 17A:
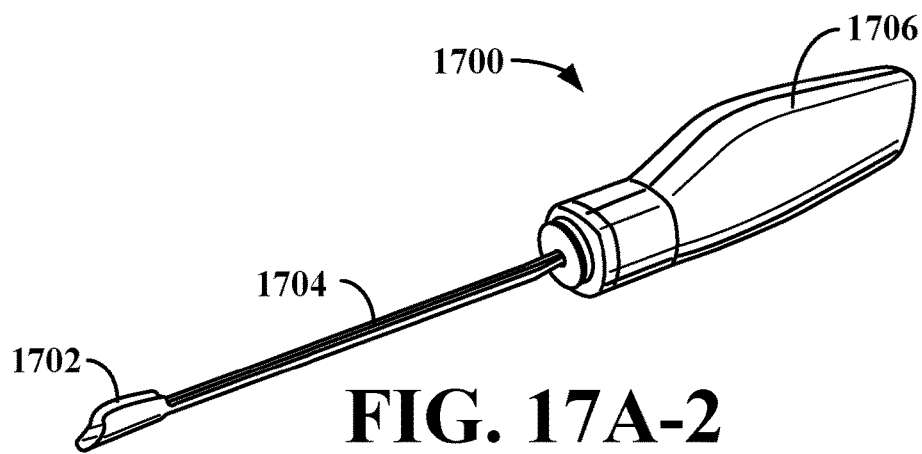
Figure 17B:
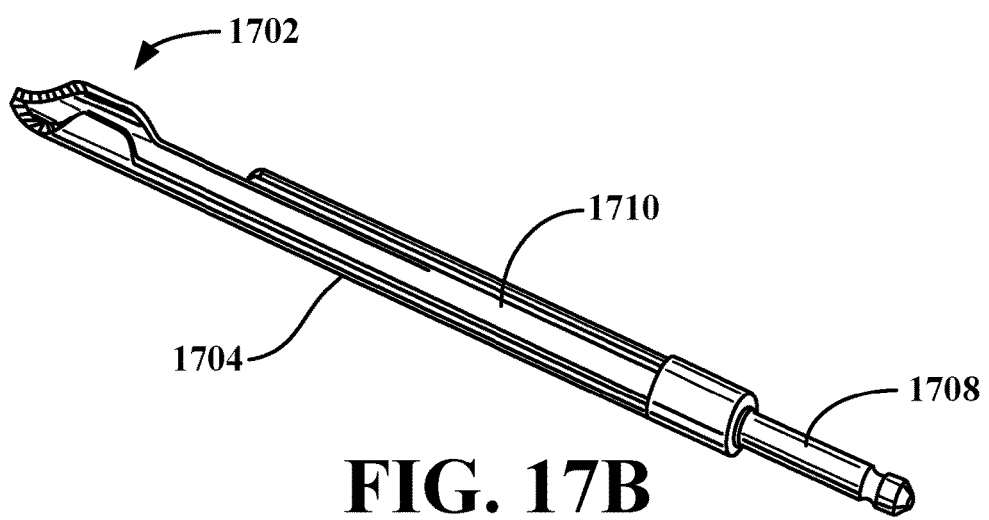
Figure 17C:
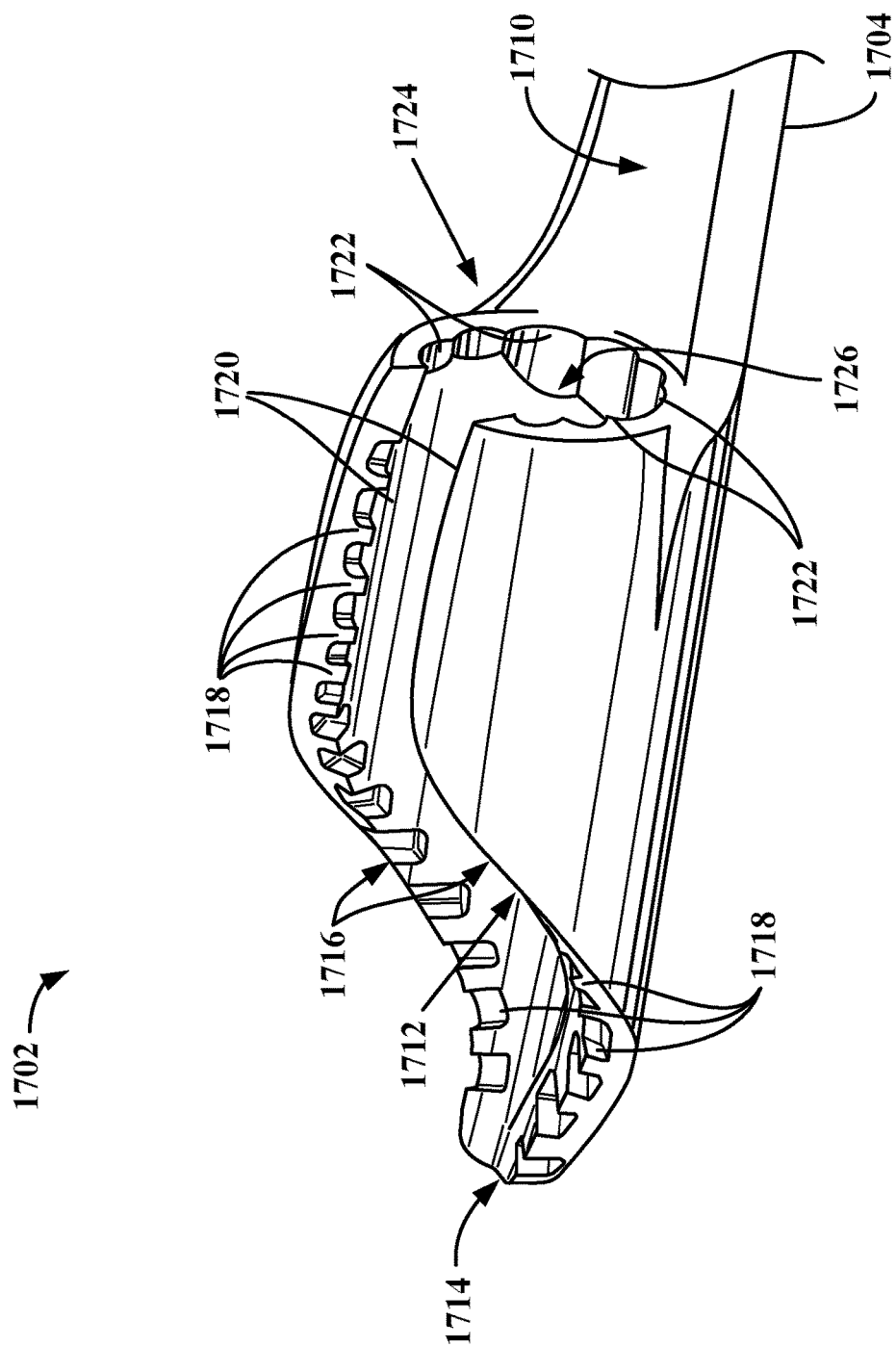

FIG. 17C provides a detailed view of the removal head 1702. The removal head 1702 preferably has a tip 1714 which is preferably blunt or atraumatic at the distal end to protect the patient from injury during device insertion. A "V"-shaped cutting edge 1716 is formed just proximal to the blunt tip 1712 and has a plurality of serrations or equivalent cutting features 1718 formed therein. The cutting features will assist in dissecting the peri-cuff tissues as the device 1700 is advanced over the catheter, as described in more detail with respect to FIGS. 20A-20F. The serrations or other cutting features 1718 may optionally continue along the upper edges or "wings" 1720 of the removal head 1702 which lie axially along each side of the groove or passage 1712. These additional cutting features can facilitate complete dissection of the cuff from the surrounding tissue.

The groove or channel 1712 through the removal head 1702 will typically be enlarged relative to the groove 1710 through the shaft to form a "receptacle" to receive the catheter cuff after the cuff has been dissected from surrounding tissue and prior to encountering additional serrations or other cutting features 1722 on a proximal surface 1724 of the removal head 1702. The proximal surface 1724 results from a tapering of the proximal portion 1728 of the head, forming an opening 1726 which is intentionally undersized in relation to the catheter and cuff.

After the removal head 1702 is advanced distal to the catheter cuff (as illustrated in FIGS. 20A-20F), the device 1700 may be retracted proximally to engage the proximal surface 1724 against the cuff. The cutting features 1722 may then be used to fragment the scar sheath from the cuff and catheter. The serrations or other cutting features 1718 and 1724 are illustrated in this embodiment of the device but may be replaced with other more aggressive cutting element or with smooth surface. The removal head 1702 is shown to be fused to (integral with) the shaft 1708 and provides a distinct active element. The shaft 1704 is only used to push and pull the removal head 1702 along the catheter.

The cutting elements 1718 on the V-shaped cutting edges 1716 function with forward pressure which allows for cutting of the scar tissue surrounding the catheter cuff. The cutting elements 1722 on the upper edges 1720 are perpendicular to cutting line of the forward cutting elements 1718 which is important since scar tissue is never perfectly shaped in a single direction. The change in serration angles with blade movement can thus optimize dissection. While cutting may be achieved by advancing the blade surface at 90 degrees relative to the tissue, cutting and dissection can be achieved at many other angles as well.

The receptacle formed by the passage 1712 in the removal head 1702 is situated in the middle of the removal head, where the cuff, once dissected from the surrounding tissue, comes to rest during forward movement of the device 1700. This occurs after the cuff is cut free from surrounding tissue and precedes cutting of the scar sheath surrounding the more central portion of the existing catheter. Upon completion of the forward dissection process, the cuff will lie adjacent the receptacle which has an opening used for insertion of the catheter into the head. The upper edges or wings 1720 of the removal head 1702, situated above the cuff receptacle in passage 1712, cut any remaining scar on the cuff's distal side typically by rotating the removal head about its axis over the catheter body and/or cuff.

The cutting features 1722 over the opening in the proximal surface 1724 have a smaller cross-sectional area than those of the catheter and cuff. The passage 1712 tapers in the proximal direction so that forward motion of the device, and traction on the catheter, causes the proximal surface 1724 to compresses the cuff and then the catheter as the removal head 1702 moves along the catheter. The cuff then slips past the opening in the proximal surface. When present, the cutting features 1722 allow rotational cutting of the dense scar material surrounding the catheter near the cuff. Traction on the device 1700 causes the proximal cutting features 1722 to wedge against the base of the cuff. The device is restricted from slipping back over the overall shape of the head allows for dilation of the skin opening around the catheter. In addition, the dissection point angles toward the central axis line to further facilitate moving the point under the scar and closer to the cuff's base. With traction and concomitant rotational motion of the device, the device and catheter are removed as a unit from the body and hemostasis obtained with direct pressure.

Figure 17D:
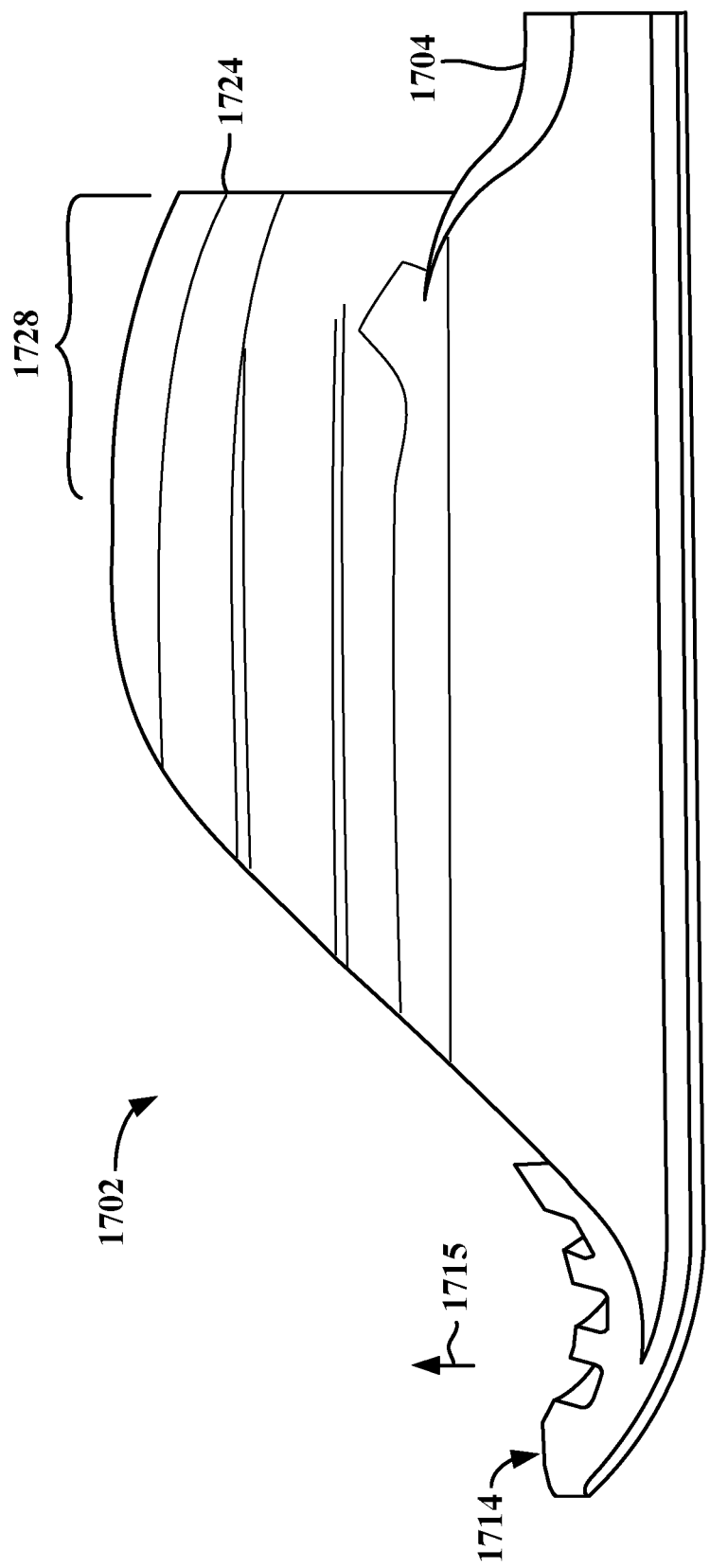

FIG. 17D shows a side view of the removal head 1702. The outside of the removal head is preferably polished metal or smooth plastic and allows low-friction passage through the subdermal tissues. The distal tip of the head 1714 is preferably pointed or curved radially inwardly and is used for blunt dissection of the peri-cuff tissues. It also facilitates a low-resistance passage of the removal head through the skin at the catheter exit site. The tapered proximal portion 1726 of the removal head provides a smaller proximal surface 1724. The removal head is shown to be fused to the shaft 1704 but remains a separate unique component of the device. While the shaft 1704 is shown as a grooved structure to accommodate and follow the catheter, it will be appreciated that the shaft could be a simple rod or other elongated structure so long as it can advance and retract the removal head along the implanted catheter.

Figure 18A:
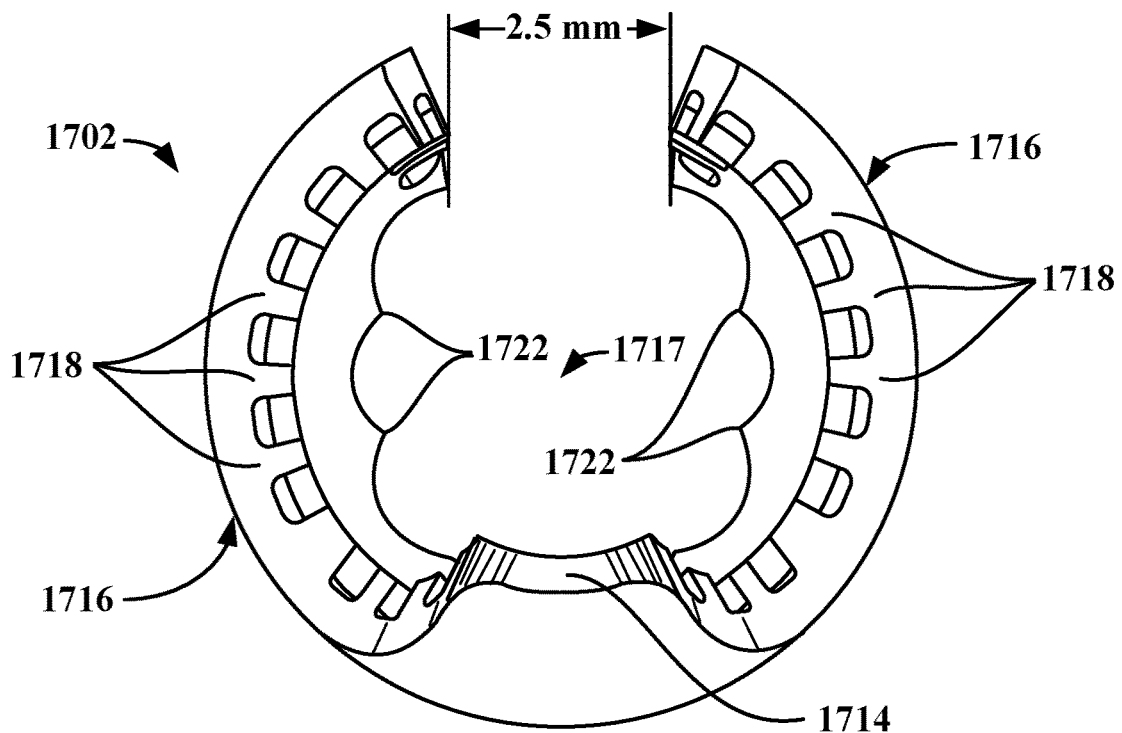
FIGS. 18A-18C show exemplary dimensions for the removal heads of the present invention.
Figure 18B:
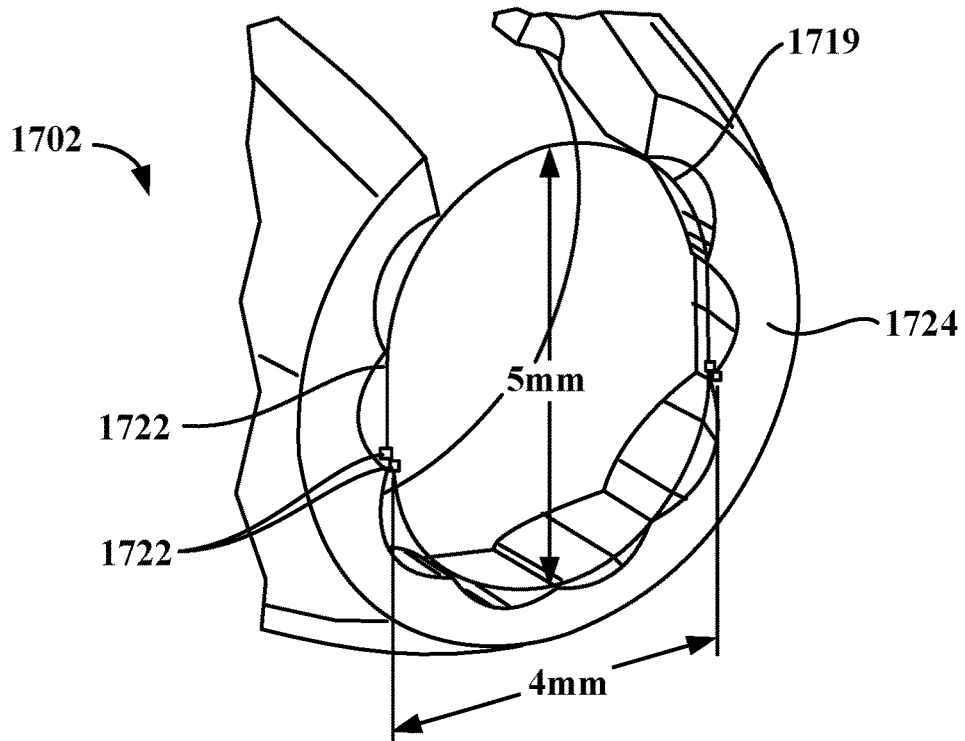
Figure 18C:
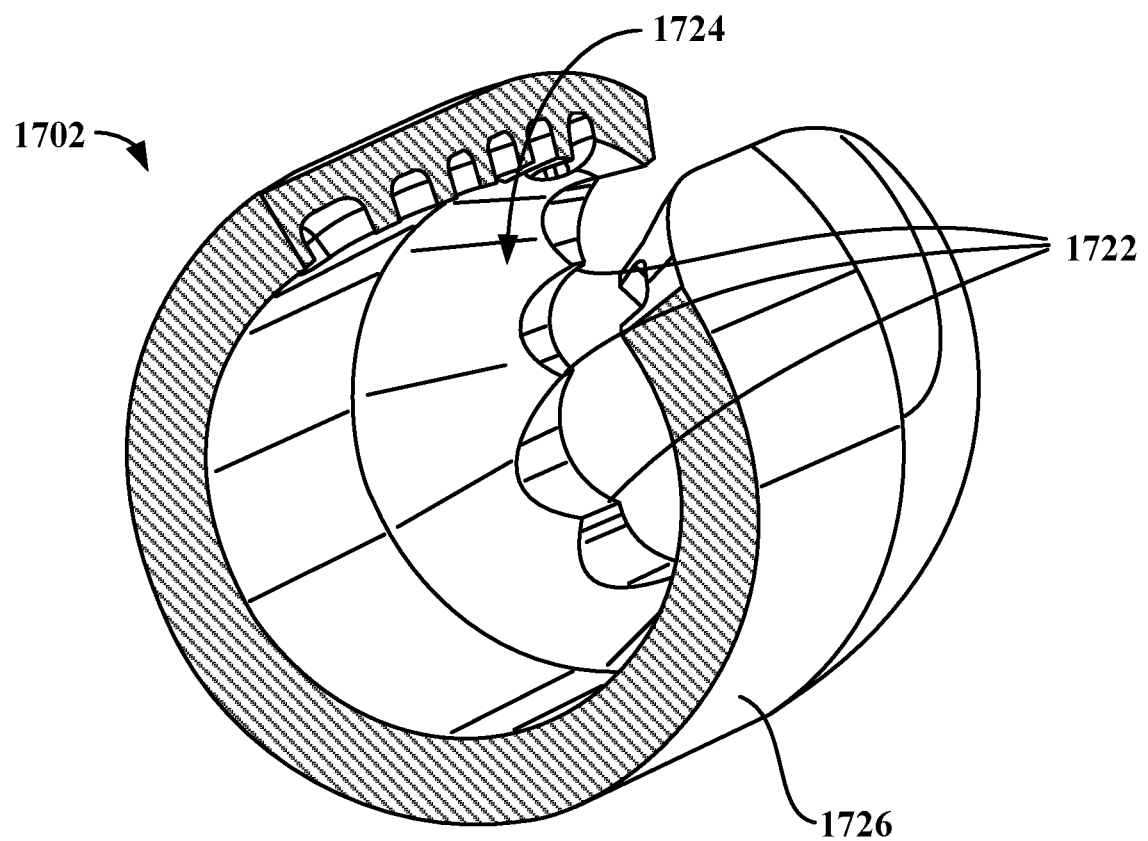

FIGS. 18A-18C provide further views of the removal head 1702 of FIGS. 17A-17D where the shaft 1704 has been removed from the head. FIG. 18A shows a front view looking along a distal-to-proximal axis. The cutting features 1718 on the V-shaped cutting edge 1716 and the cutting features 1722 on the proximal surface 1724 can both be seen, and the smaller size and oblong geometry of the proximal opening 1726 is clearly visible. FIG. 18A shows an exemplary dimension (2.5 mm) of the spacing of the wings 1720, and FIG. 18B shows exemplary dimensions (in mm) of the proximal opening of the removal head. The dimensions are provided as examples only and may be varied based upon the size of the catheter or to alter functionality.

FIG. 18C shows a cross-sectional view facing proximally, with the proximal cutting surface 1724 visible. The conical taper of the proximal portion 1726 of the head leading to the proximal surface 1724 is visible from this view.

Figure 19:
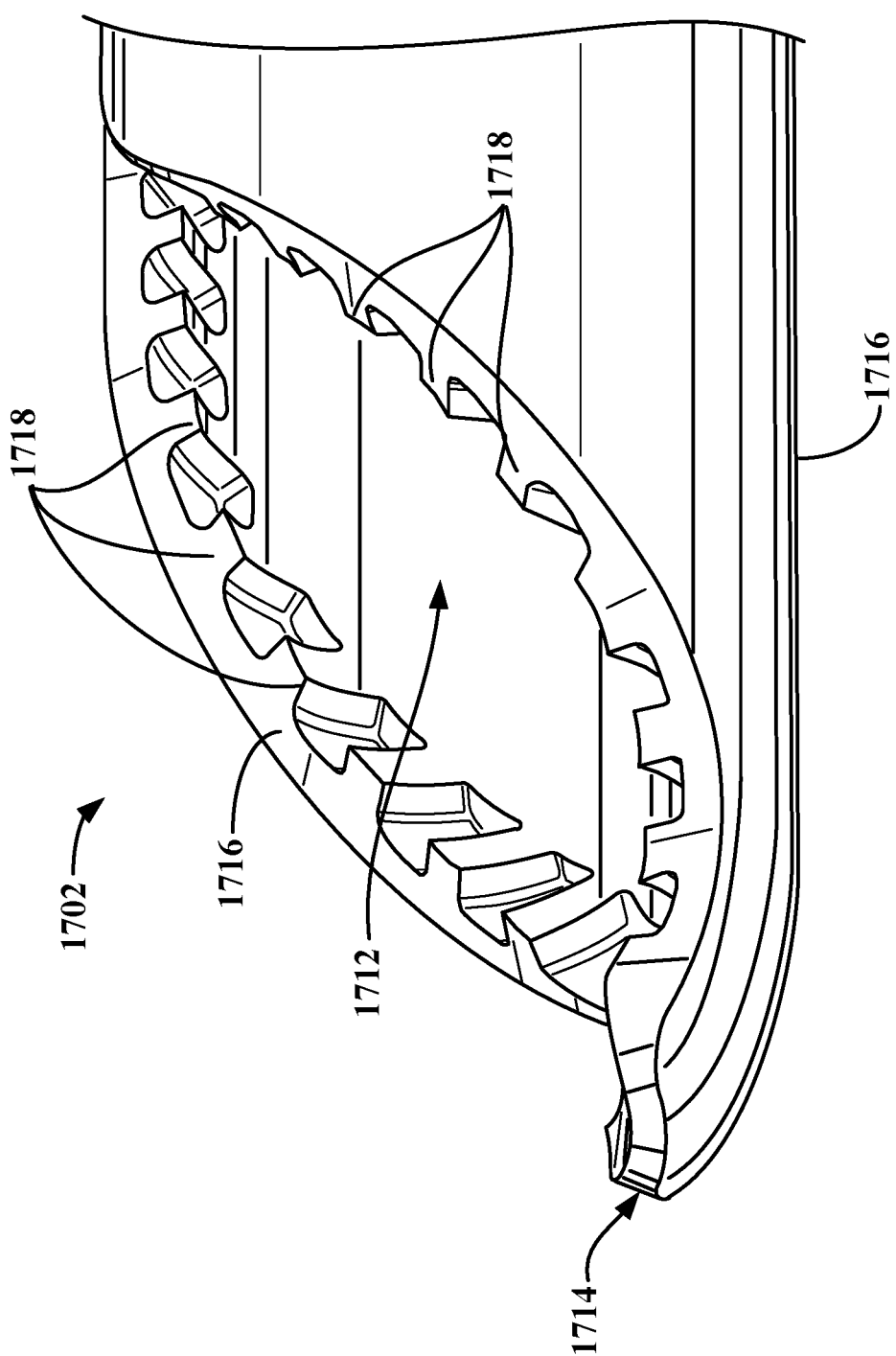
FIG. 19 shows an oblique view of a further exemplary distal cutting element of the removal head of the present invention.

FIG. 19 shows an oblique view of the distal cutting element of the removal head 1702. The tip 1714 has a flattened or "blunt" tip, tapering toward midline. The blunt tip allows for safe but aggressive dissection of peri-cuff tissues. The "V" shaped cutting element 1716 on the distal portion of the head of the device is also shown.

FIGS. 20A-20F show a method according to the present invention where the device 1700 is used to advance and retract the removal head over the catheter and cuff of an implanted cuffed catheter. For ease of description, the shaft is not illustrated since it is used only to manipulate the removal head and is not an active element in dissection of the catheter and cuff.

Figure 20A:
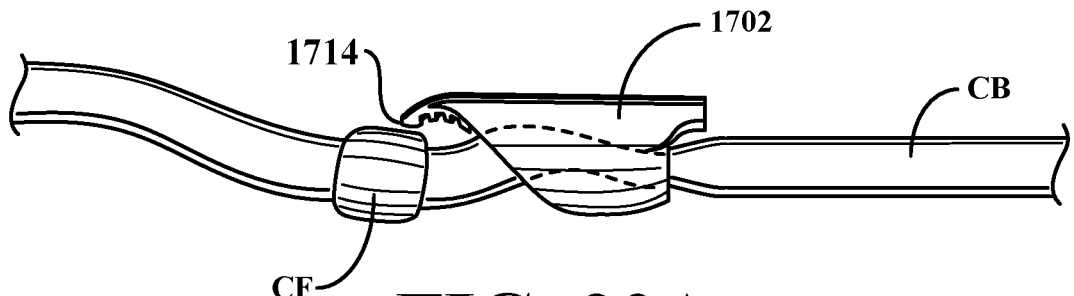
FIGS. 20A-20F shows a method of using the device of the present invention for capturing and dislodging a cuff on a central cuffed catheter in accordance with the principles of the present invention.
Figure 20B:
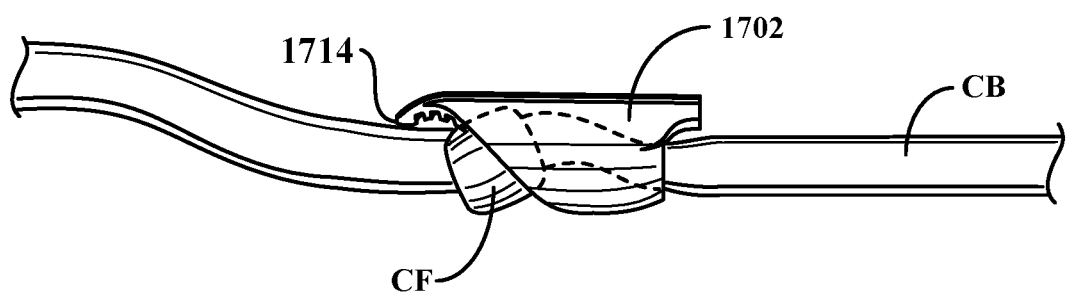
Figure 20C:
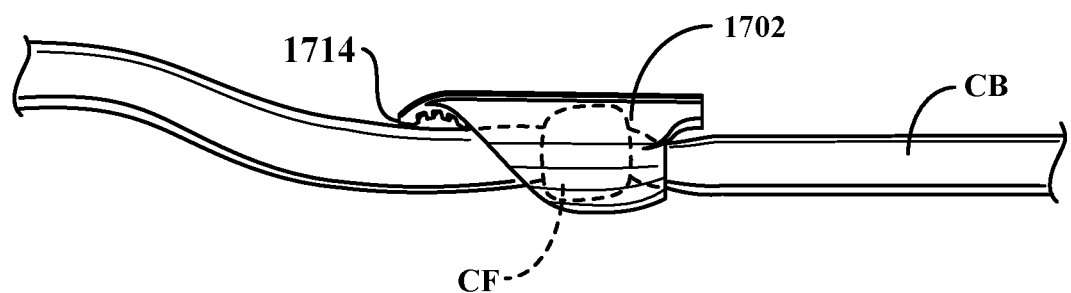
Figure 20D:
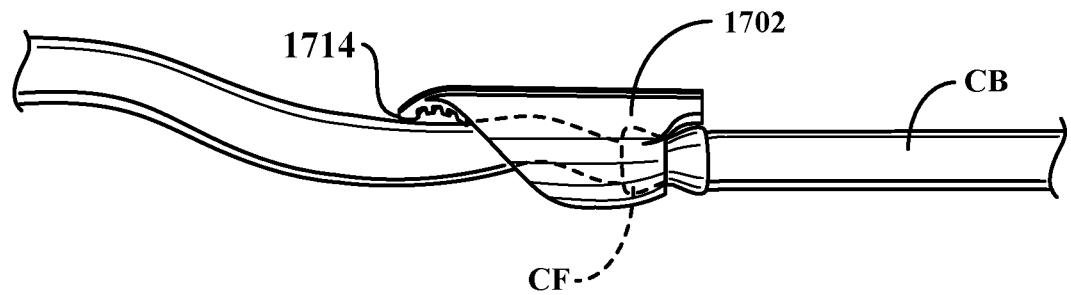
Figure 20E:
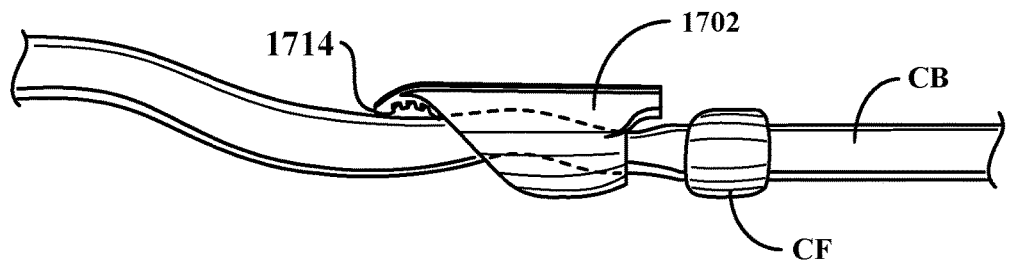
Figure 20F:
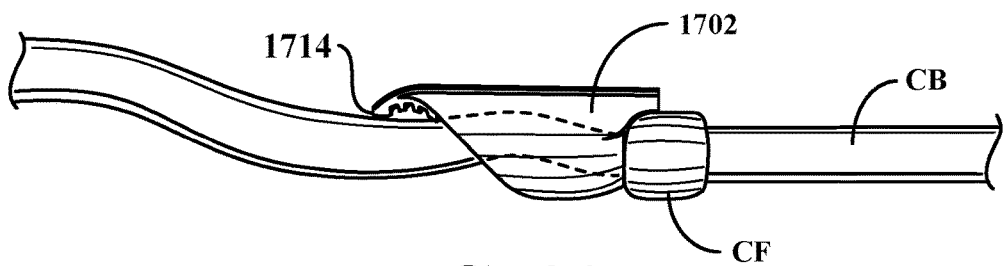

Use of the device 1700 begins with placing the external portion of the catheter into the central passage 1712 of removal head 1702 (FIG. 20A). The removal head is then advanced along the catheter. The head of the device is used to dilate the skin opening and the device is passed into the subdermal location. The blunt tip 1714 of the removal head is used to dissect the peri-cuff tissues, and then the "V" shaped cutting edge 1716 is advanced to dissect the cuff from surrounding tissues using forward pressure. After the cuff is dissected away from the subdermal tissues, the cuff comes to rest in the "receptacle" of the passage 1712 in the removal head 1702 (FIG. 20C). Further advancement of the device 1700 along the catheter causes compression of the cuff and catheter by the proximal cutting elements 1722 (FIG. 20D). Once the removal head 1702 has passed beyond the cuff, traction is placed on a proximal the device 1700 (which extends from the tissue tract), bringing the proximal cutting elements 1722 into contact with the cuff (FIG. 20F). With gentle rotation and traction, fracture of the scar sheath from around the catheter is accomplished, and the device and catheter can removed as a single unit.

FIG. 20A shows the tip 2000 of the head 2003 as used to dissect over the catheter cuff 2001. The proximal cutting element 2002 provides mild compression of the catheter as it is advanced into the patient. FIG. 20B demonstrates the "V" shaped distal cutting element as it would be passed over the cuff to disconnect the cuff from surrounding subdermal tissues. Although V is the preferred shape, any shape that allows the head to slip through the peri-cuff and begin dissection without causing trauma to the patient is also disclaimed. FIG. 20C shows the position of the head of the device 2003 after full dissection of the cuff from surrounding tissues. The cuff 2001 is sitting inside the head in the reception area of the head (see FIG. 17A; 1702). FIG. 20D shows the position of the cuff 2001 after entering the conical proximal portion of the head. The cuff is compressed by the oblong opening of the proximal cutting surface 2002. FIG. 20E shows the position of the head 2003 after advancement of the proximal cutting surface 2002 beyond the cuff of the catheter. Note compression of the catheter by the proximal cutting surface 2002 of the removal head. FIG. 20F shows the position of the head 2003 in relation to the cuff 2001 on the catheter when traction is placed on the device. The proximal cutting surface 2002 is apposed to the base of the cuff 2001 along the catheter and is used to cut the scar sheath around the catheter. With further traction on the device, the scar sheath is fractured and the device and catheter can be removed through the skin exit site as a single unit.

Figure 21:
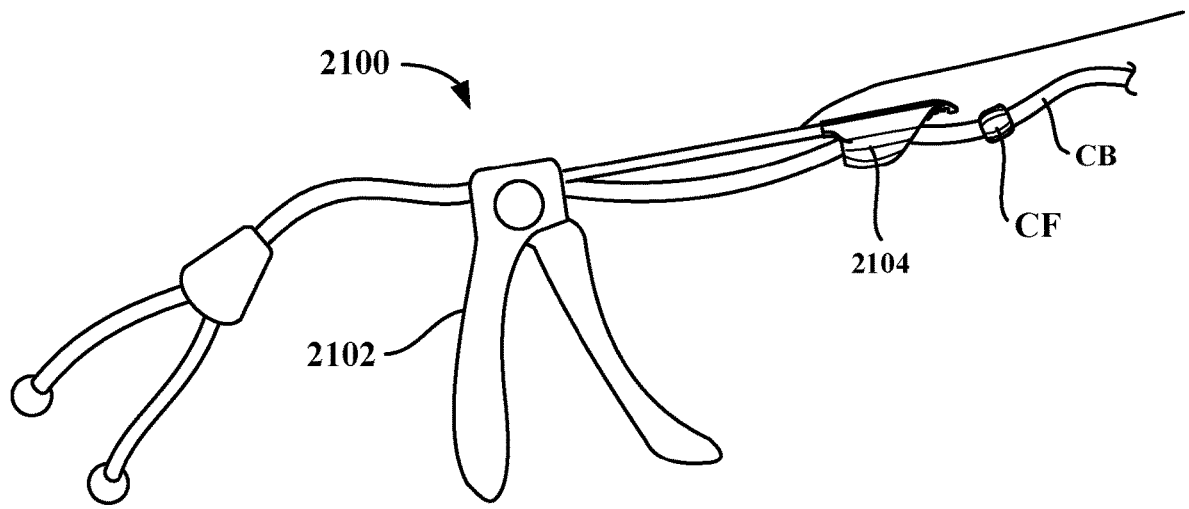
FIG. 21 shows a further exemplary embodiment of the device of the present invention having a ratcheting handle.

As a further embodiment, the device may include a system to facilitate advancement of the device along the catheter for ease in dissection of the peri-cuff tissues. For example, a manual or electrically powered ratcheting mechanism can provide repetitive compression of a handle to incrementally advance the device over the catheter and cuff. After the device is successfully beyond the cuff, it is released from the ratcheting mechanism and the device retracted, bringing the proximal portion of the head into contact with the cuff as previously described. This incremental advancement system may be alternatively accomplished with a screw-drive mechanism or other similar mechanical or electro-mechanical system. These alternatives are also included under the umbrella of this invention FIG. 21 shows an embodiment of the device with a ratcheting handle. This handle 2101 affixes to the catheter 2100 and incrementally advances the device shaft and head 2102 along the catheter. The head of the device then encounters the cuff 2104. Once beyond the cuff, the ratcheting handle is released from the catheter and the proximal cutting element engaged to cut the scar sheath on the catheter. The device and catheter are then removed as a unit with gentle traction. A ratcheting handle variant uses a variable length shaft which moves the head either forward or backward upon actuation. A toggle switch controls direction. As the head moves to the cuff, the same method as previously described can be used to dissect peri-cuff scar tissues. Once free, the device and catheter are removed as a unit with gentle traction.

The foregoing discussion discloses and describes merely exemplary methods and embodiments. As will be understood by those familiar with the art, the disclosed subject matter may be embodied in other specific forms without departing from the spirit or characteristics thereof. Accordingly, the present disclosure is intended to be illustrative, but not limiting, of the scope of the invention, which is set forth in the following claims.

What is claimed is:

1. A tool for removing an implanted catheter wherein the implanted catheter has a catheter body and a cuff, said tool comprising:
a removal head including a tubular body having a distal opening, a proximal opening configured to be secured to a distal end of an elongated manipulator, and an axial opening extending from the distal opening to the proximal opening along one side of the tubular body, said axial opening configured to be placed over the catheter body;
wherein the proximal opening has cutting features over an interior edge thereof;
wherein said tubular body has a blunt distal tip and first and second cutting edges extending obliquely in a proximal direction from the blunt distal tip.

2. A tool as in claim 1, further comprising cutting elements formed along the first and second cutting edges.

3. A tool as in claim 2, wherein the cutting elements are serrations.

4. A tool as in claim 1, wherein the first and second cutting edges are swept back at an angle generally from 30° to 60°.

5. A tool as in claim 1, wherein the tubular body has third and fourth cutting edges along the axial opening, wherein the third and fourth cutting edges are oriented to cut tissue as the removal head is rotatable over the catheter body or the cuff.

6. A tool as in claim 5, further comprising cutting elements along the third and fourth cutting edges.

7. A tool as in claim 6, wherein the cutting elements are serrations.

8. A tool as in claim 1, wherein the removal head is tapered in the proximal direction and the proximal opening has an area smaller than a cross-sectional area of distal regions of an interior volume of the removal head.

9. A tool as in claim 8, wherein the proximal opening has an oblong periphery.

10. A tool as in claim 1, further comprising the elongated manipulator.

11. A tool as in claim 10, wherein the elongated manipulator comprises a shaft and a handle.

12. A tool as in claim 11, wherein the removal head is integrally formed with the shaft.

13. A tool as in claim 12, wherein the shaft has an axial channel configured to receive the catheter body as the removal head is advanced over the catheter body.

14. A tool as in claim 13, wherein the shaft comprises a stem which is removably attached to the handle.

* * * * *